(12) United States Patent
Martinek et al.

(10) Patent No.: US 7,645,293 B2
(45) Date of Patent: Jan. 12, 2010

(54) SUTURE ANCHOR INSTALLATION SYSTEM AND METHOD

(75) Inventors: Jonathan Martinek, Hamden, CT (US); Stephen Zlock, Redding, CT (US); Hanspeter R. Bayer, Meriden, CT (US); Peter Barreiro, West Haven, CT (US); Pat A. Libero, Jr., North Haven, CT (US)

(73) Assignee: United States Surgical Corporation, North Haven, CT (US)

( * ) Notice: Subject to any disclaimer, the term of this patent is extended or adjusted under 35 U.S.C. 154(b) by 433 days.

(21) Appl. No.: 11/108,269

(22) Filed: Apr. 18, 2005

(65) Prior Publication Data

US 2005/0240199 A1  Oct. 27, 2005

(51) Int. Cl.
*A61B 17/04* (2006.01)

(52) U.S. Cl. ..................................................... 606/232
(58) Field of Classification Search ............. 606/72–74, 606/232–233
See application file for complete search history.

(56) References Cited

U.S. PATENT DOCUMENTS

| | | | |
|---|---|---|---|
| 4,772,286 A | 9/1988 | Goble et al. | |
| 4,870,957 A | 10/1989 | Goble et al. | |
| 4,899,743 A | 2/1990 | Nicholson et al. | |
| 4,927,421 A | 5/1990 | Goble et al. | |
| 4,946,468 A | 8/1990 | Li | |
| 4,950,270 A | 8/1990 | Bowman et al. | |
| 4,989,614 A * | 2/1991 | Dejter et al. ................. | 600/565 |
| 5,037,422 A | 8/1991 | Hayhurst et al. | |
| 5,100,417 A | 3/1992 | Cerier et al. | |
| 5,139,520 A | 8/1992 | Rosenberg | |
| 5,152,790 A * | 10/1992 | Rosenberg et al. ....... | 623/13.14 |
| 5,156,616 A | 10/1992 | Meadows et al. | |
| RE34,293 E | 6/1993 | Goble et al. | |
| 5,258,016 A | 11/1993 | DiPoto et al. | |
| 5,320,115 A | 6/1994 | Kenna | |
| 5,354,298 A * | 10/1994 | Lee et al. ....................... | 606/72 |
| 5,370,662 A | 12/1994 | Stone et al. | |
| RE34,871 E | 3/1995 | McGuire et al. | |
| 5,400,902 A * | 3/1995 | Kaminski ................... | 206/310 |
| 5,443,482 A | 8/1995 | Stone et al. | |

(Continued)

FOREIGN PATENT DOCUMENTS

EP    834281 A    4/1998

(Continued)

OTHER PUBLICATIONS

European Search Report for EP 05 00 8751, date of Completion of the search Oct. 21. 2005 (6 pgs).

(Continued)

*Primary Examiner*—(Jackie) Tan-Uyen T. Ho
*Assistant Examiner*—Gregory A Anderson

(57) ABSTRACT

An apparatus for placement of a suture anchor having a suture connected thereto includes a handle dimensioned for engagement by the user and an elongated member connected to the handle and extending therefrom. The elongated member has an anchor mount for mounting a suture anchor. The handle includes a frame having a suture retainer adapted for retaining a suture, at least one cover releasably mounted to the frame to at least partially enclose the suture retainer and a release button mounted to the frame and movable to release the at least one cover from the frame to expose the suture portion.

34 Claims, 18 Drawing Sheets

U.S. PATENT DOCUMENTS

| | | | |
|---|---|---|---|
| 5,443,509 A | 8/1995 | Boucher et al. | |
| 5,505,735 A * | 4/1996 | Li | 606/72 |
| 5,571,139 A | 11/1996 | Jenkins, Jr. | |
| 5,573,548 A | 11/1996 | Nazre et al. | |
| 5,584,860 A | 12/1996 | Goble et al. | |
| 5,601,557 A | 2/1997 | Hayhurst | |
| 5,645,547 A | 7/1997 | Coleman | |
| 5,662,654 A | 9/1997 | Thompson | |
| 5,690,489 A | 11/1997 | Carchidi | |
| 5,690,676 A | 11/1997 | DiPoto et al. | |
| 5,697,931 A | 12/1997 | Thompson | |
| 5,707,394 A | 1/1998 | Miller et al. | |
| 5,733,307 A | 3/1998 | Dinsdale | |
| 5,782,862 A | 7/1998 | Bonutti | |
| 5,782,866 A | 7/1998 | Wenstrom, Jr. | |
| 5,797,914 A | 8/1998 | Leibinger | |
| 5,814,051 A | 9/1998 | Wenstrom, Jr. | |
| 5,814,070 A | 9/1998 | Borzone et al. | |
| 5,868,789 A | 2/1999 | Huebner | |
| 5,871,486 A | 2/1999 | Huebner et al. | |
| 5,904,704 A | 5/1999 | Goble et al. | |
| 5,944,724 A | 8/1999 | Lizardi | |
| 5,944,739 A | 8/1999 | Zlock et al. | |
| 5,948,000 A | 9/1999 | Larsen et al. | |
| 5,948,001 A | 9/1999 | Larsen | |
| 5,993,459 A | 11/1999 | Larsen et al. | |
| 6,007,566 A | 12/1999 | Wenstrom, Jr. | |
| 6,045,573 A | 4/2000 | Wenstrom, Jr. et al. | |
| 6,086,608 A | 7/2000 | Ek et al. | |
| 6,117,162 A | 9/2000 | Schmieding et al. | |
| 6,139,565 A | 10/2000 | Stone et al. | |
| 6,183,479 B1 | 2/2001 | Tormala et al. | |
| 6,200,329 B1 | 3/2001 | Fung et al. | |
| 6,214,031 B1 | 4/2001 | Schmieding et al. | |
| 6,235,057 B1 | 5/2001 | Roger et al. | |
| 6,241,723 B1 * | 6/2001 | Heim et al. | 606/34 |
| 6,283,973 B1 | 9/2001 | Hubbard et al. | |
| 6,336,940 B1 | 1/2002 | Graf et al. | |
| 6,371,124 B1 | 4/2002 | Whelan | |
| 6,379,361 B1 | 4/2002 | Beck, Jr. et al. | |
| 6,387,129 B2 | 5/2002 | Rieser et al. | |
| 6,436,124 B1 | 8/2002 | Anderson et al. | |
| 6,461,373 B2 | 10/2002 | Wyman et al. | |
| 6,527,794 B1 | 3/2003 | McDevitt et al. | |
| 6,562,071 B2 | 5/2003 | Jarvinen | |
| 6,653,563 B2 | 11/2003 | Dreyfuss | |
| 6,660,023 B2 | 12/2003 | McDevitt et al. | |
| 2002/0147463 A1 * | 10/2002 | Martinek | 606/232 |
| 2003/0130695 A1 | 7/2003 | McDevitt et al. | |
| 2003/0204195 A1 | 10/2003 | Keane et al. | |

FOREIGN PATENT DOCUMENTS

| | | |
|---|---|---|
| EP | 835640 A | 4/1998 |
| EP | 1300115 A | 4/2003 |
| WO | WO 02/051325 | 7/2002 |
| WO | WO2005/102190 A | 11/2005 |

OTHER PUBLICATIONS

European Search Report for corresponding EP 08021283 date of mailing is Feb. 24, 2009 (3 pages).

European Search Report for corresponding EP 08021283 date of mailing is Jul. 22, 2009 (3 pages).

* cited by examiner

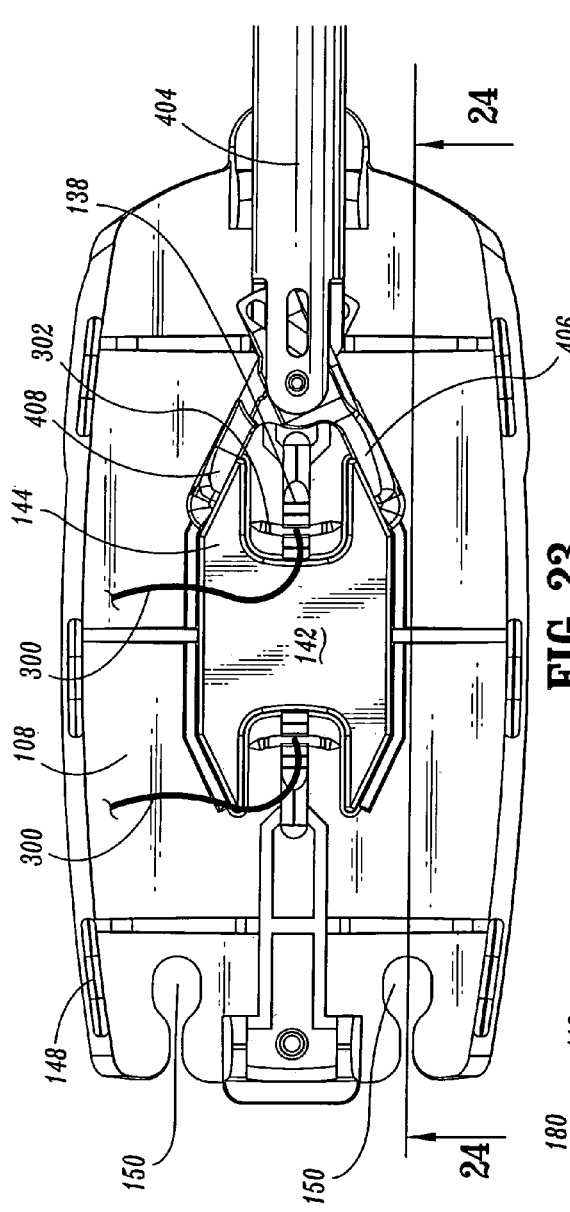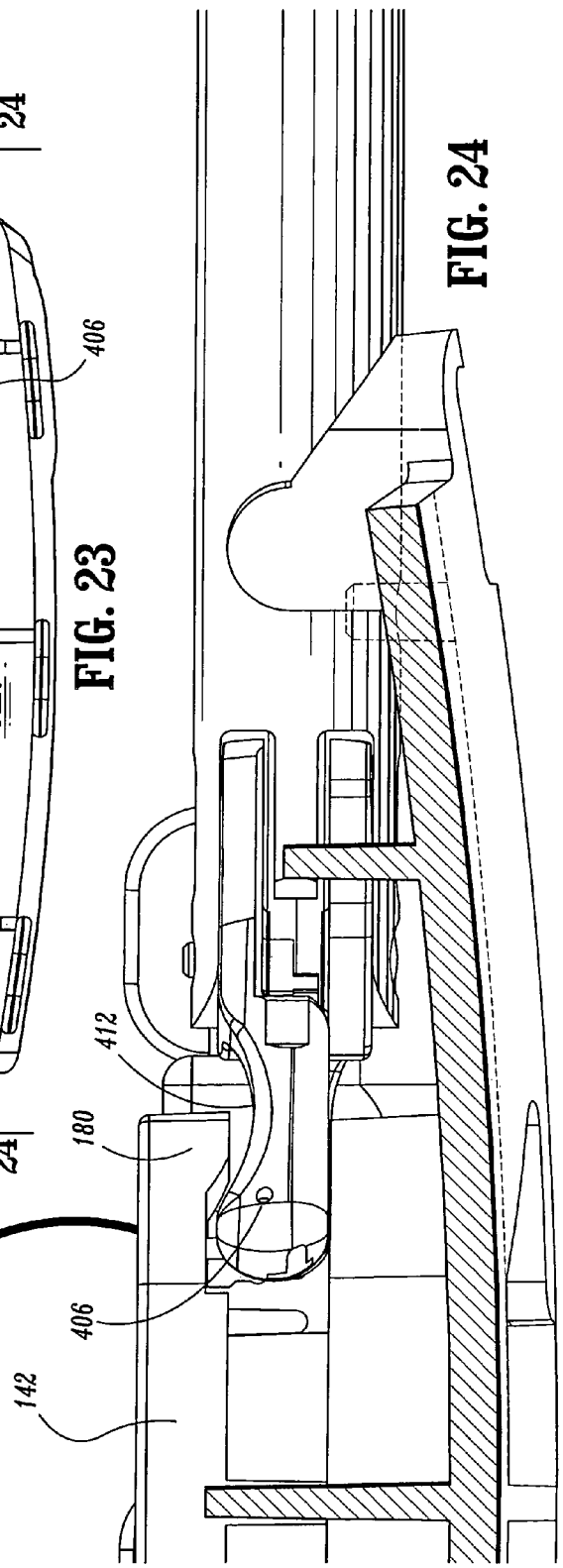

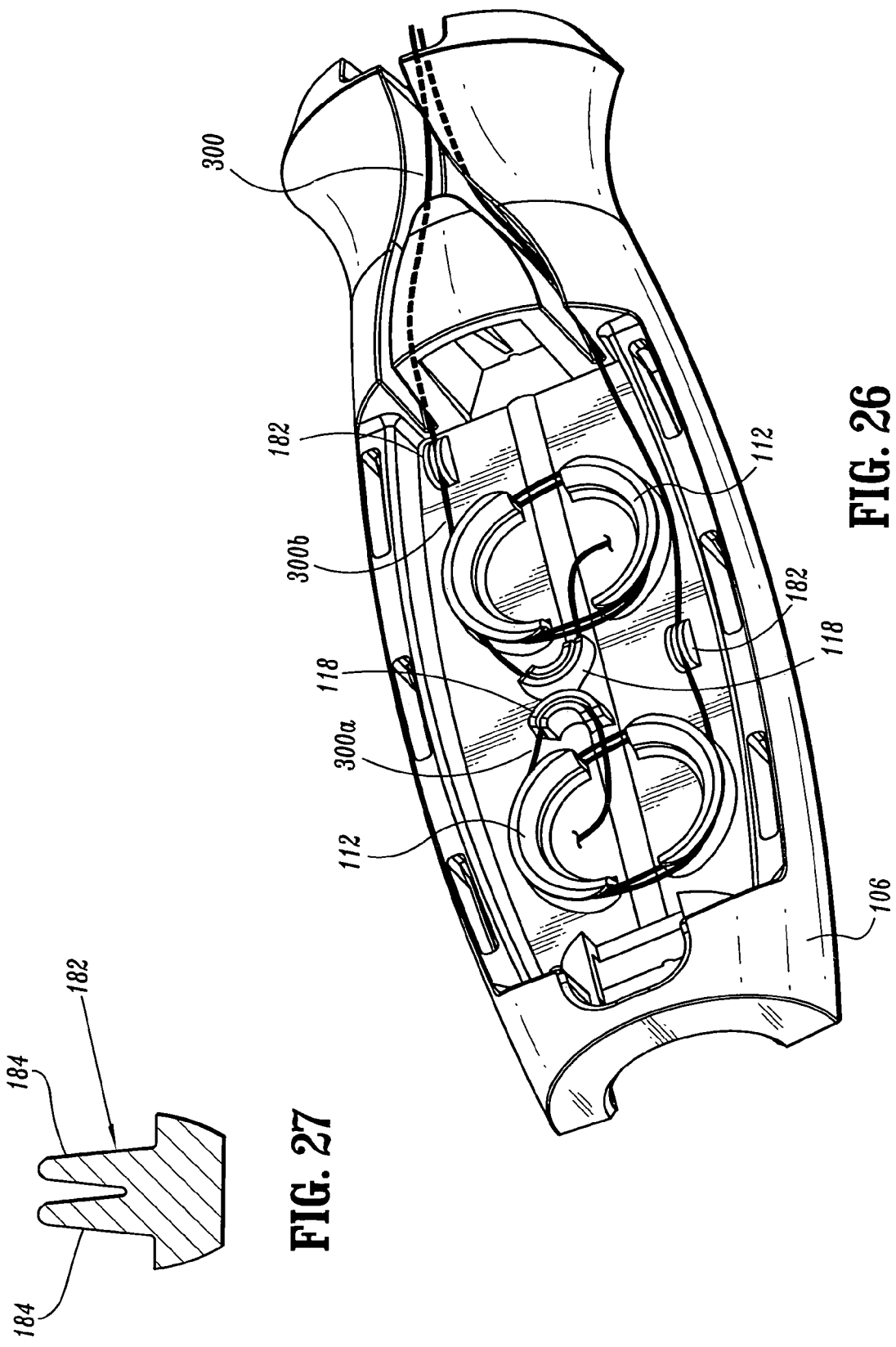

SUTURE ANCHOR INSTALLATION SYSTEM AND METHOD

BACKGROUND

1. Field of the Disclosure

The present disclosure generally relates to the surgical repair of tissue and, more particularly, relates to a system and method for installation of a suture anchor for the surgical repair of tendons, ligaments, muscle, etc.

2. Description of Related Art

Suture anchors are commonly used to attach soft and hard tissue to bone. Typically, an anchor is implanted into a drilled bore in bone mass. One or more sutures with attached needles are connected to the suture anchor. The suture is passed through the tissue and subsequently tied to secure the tissue to the bone. Over a period of time, healing occurs whereby the tissue naturally reattaches itself to the bone. In certain procedures, the suture anchors are placed temporarily to optimize the particular surgery being performed. Suture anchors find particular application in joint reconstruction surgery especially for attachment of ligaments or tendons within the knee, shoulder and elbow areas.

SUMMARY

Accordingly, the present disclosure is directed to an apparatus for placement of a suture anchor having a suture connected thereto. The apparatus includes a handle dimensioned for engagement by the user and an elongated member connected to the handle and extending therefrom. The elongated member has an anchor mount for mounting a suture anchor. The handle includes a frame having a suture retainer adapted for retaining a suture and at least one cover releasably mounted to the frame to at least partially enclose the suture retainer. A release button may be mounted to the frame and is movable to release the at least one cover from the frame to expose the suture portion. The handle may include a latch operatively connected to the release button. The latch is released upon movement of the release button. Preferably, the latch is engagable with a locking shelf of the at least one cover in a first unactuated position of the release button to secure the cover to the frame. The latch is adapted to release the locking shelf upon movement of the release button to a second actuated position thereof. The at least one cover includes a leaf spring adapted to bias the latch into engagement with the locking shelf in the first unactuated position of the release button. The release button includes a camming surface, engagable with the leaf spring upon movement of the release button to the second actuated position to permit release of the locking shelf.

The at least one cover may include a needle park for securing a needle. The at least one cover may also include a drape grab for engaging a portion of a surgical drape to facilitate securement of the at least one cover to the surgical drape.

The suture retainer of the frame includes a spool wherein the suture portion is wrapped about the spool. The elongated member includes at least one longitudinal groove for accommodating a suture portion extending to the suture anchor which is mounted to the anchor mount of the elongated member. Preferably, the elongated member includes first and second longitudinal grooves.

The apparatus may include a suture anchor and at least one suture extending from the suture anchor. The suture anchor is releasably secured to the anchor mount of the elongated member. The at least one suture extends along the elongated member and is engagable with the suture retainer of the frame. A needle is connected to the at least one suture and is releasably secured within the at least one cover. Preferably, the at least one cover includes a needle park for securing the needle.

In one embodiment, the handle includes first and second suture retainers for retaining first and second suture portions and first and second covers releasably mounted to the frame for substantially enclosing respective first and second suture retainers. The release button is movable to release the first and second covers.

In an alternate embodiment, an apparatus for placement of a suture anchor having a suture connected thereto, includes a handle dimensioned for engagement by the user and an elongated member connected to the handle and extending therefrom. The elongated member has an anchor mount for mounting a suture anchor. The handle includes a frame having first and second opposed frame sections with a suture retainer adapted for retaining a suture portion, first and second covers releasably mounted to respective first and second frame sections to at least partially enclose the suture retainers and having a needle park for retaining a needle, and a release button mounted to the frame and movable to release the first and second covers to expose the suture portions.

In another preferred embodiment, a suture anchor includes an outer sleeve having a threaded portion and defining a longitudinal axis, and an inner suture pin positionable within the outer sleeve. The suture pin includes first and second bores for receiving respective first and second sutures. The bores each define a bore axis extending in transverse relation to the longitudinal axis. The suture pin includes grooves formed in an outer surface thereof and extending from respective transverse bores. The grooves are dimensioned to accommodate suture portions extending from the transverse bores. The bore axes of the first and second bores may be in general parallel relation to each other. The suture pin includes first and second pin sections having the first and second bores respectively. The first pin section defines a cross-sectional dimension greater than the second pin section. The threaded portion of the outer sleeve may include flutes defined therein. The inner suture pin includes a pin head and a pin shaft. The pin shaft has the first and second bores and at least partially positionable in the outer sleeve. The pin head has at least one chamfer defined in an outer surface thereof. Preferably, the pin head includes a pair of chamfers arranged in general diametrical opposed relation.

BRIEF DESCRIPTON OF THE DRAWINGS

Preferred embodiments of the present disclosure will be readily appreciated by reference to the drawings wherein:

FIG. 10 is an enlarged isolated view illustrating the relationship of the release latch of the release button and the leaf spring of the cover;

FIG. 23 is a top plan view illustrating positioning of the jaws of the suturing apparatus on the needle park to engage the needle attached to the suture;

FIG. 24 is an enlarged cross-sectional view taken along the lines 24-24 of FIG. 23;

FIG. 26 is a perspective view of an alternate embodiment of the handle of the installation tool;

FIG. 27 is an isolated view of the tensioning cleat of the handle of FIG. 26;

DETAILED DESCRIPTION OF THE PREFERED EMBODIMENT

The suture anchor installation system of the present disclosure is adapted to secure a suture relative to bony tissue. The suture is preferably used to attach soft tissue or a prosthetic implant to bone tissue. As used herein, the term "soft tissue" refers to all of the non-bony tissues within a body including, but not limited to, muscles, tendons, cartilage, skin, ligaments, etc. The term "prosthetic implant" refers to any article implanted in the body including, but not limited to, artificial ligaments, muscles, joints, etc.

The suture anchor installation system can be used in minimally invasive surgical procedures. In such procedures, the operating instrumentation is deployed through a cannula inserted through a small incision or opening in a wall of body tissue (e.g. the skin and underlying tissue), or directly through the incision or opening itself. Such procedures include laparoscopic, endoscopic, and arthroscopic surgical operations. In operations where, for example, a body cavity is insufflated to provide a clear operating field, gaseous seals are usually employed to prevent the inflow or egress of fluids into or out from the operating site. It should be understood that the suture anchor installation system is not limited to minimally invasive procedures, and can be used in open surgical procedures as well.

The suture anchor installation system described herein includes a suture anchor assembly retained in a suture anchor insertion tool. The suture anchor assembly features a two-piece suture anchor for insertion into a pre-drilled hole in bone and at least one suture having at least one surgical needle affixed thereto. The two-piece suture anchor includes a suture pin positionable within an outer screw sleeve which is threaded into the sides of the hole which has been drilled into the bone.

In the discussion which follows, as is traditional, the term "proximal" refers to that portion of the instrument closest to the operator while the term "distal" refers to that portion of the instrument most remote from the operator.

Figure 1:
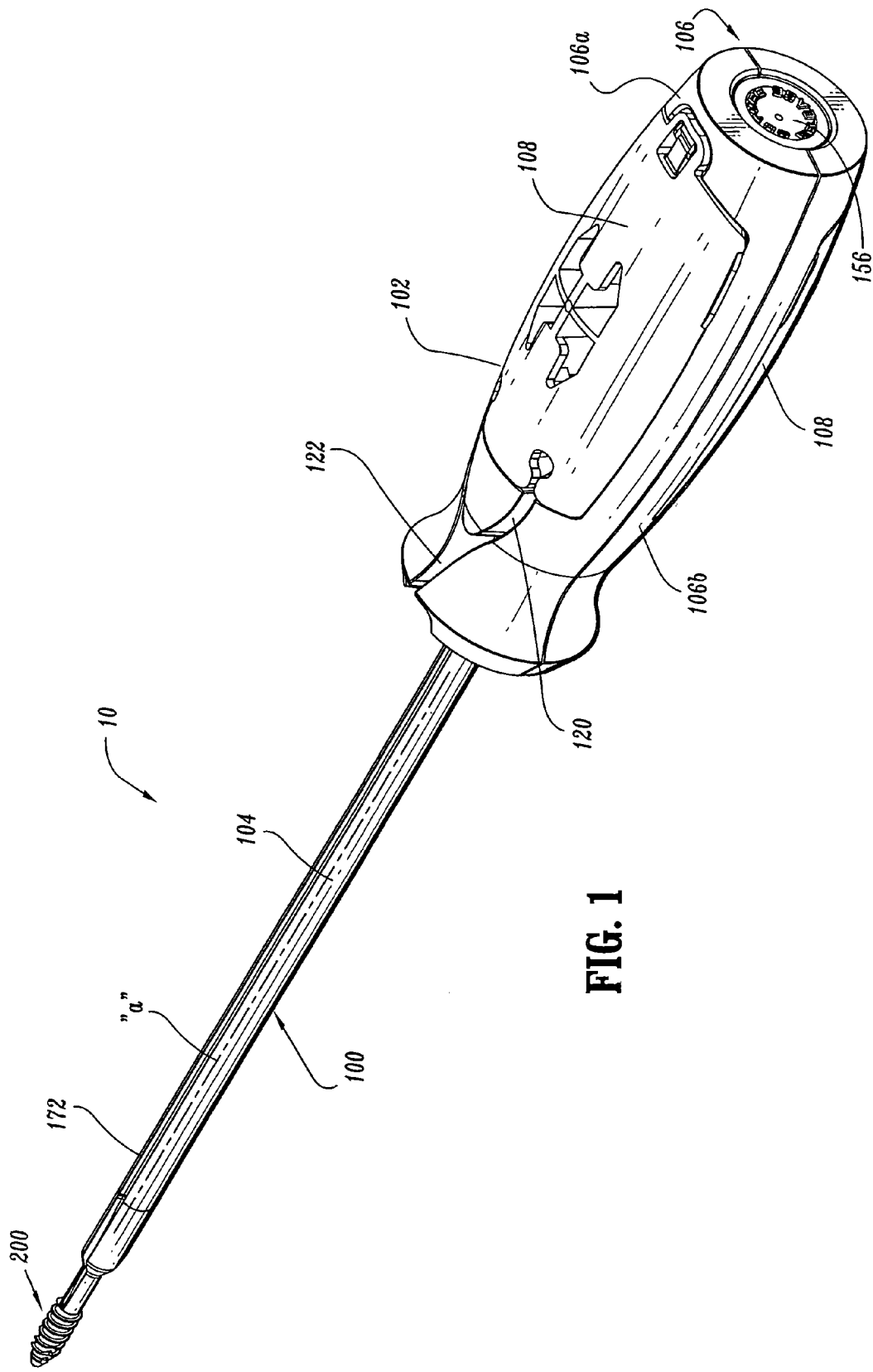
FIG. 1 is a perspective view of a suture anchor installation system in accordance with the principles of the present disclosure.
Figure 2:
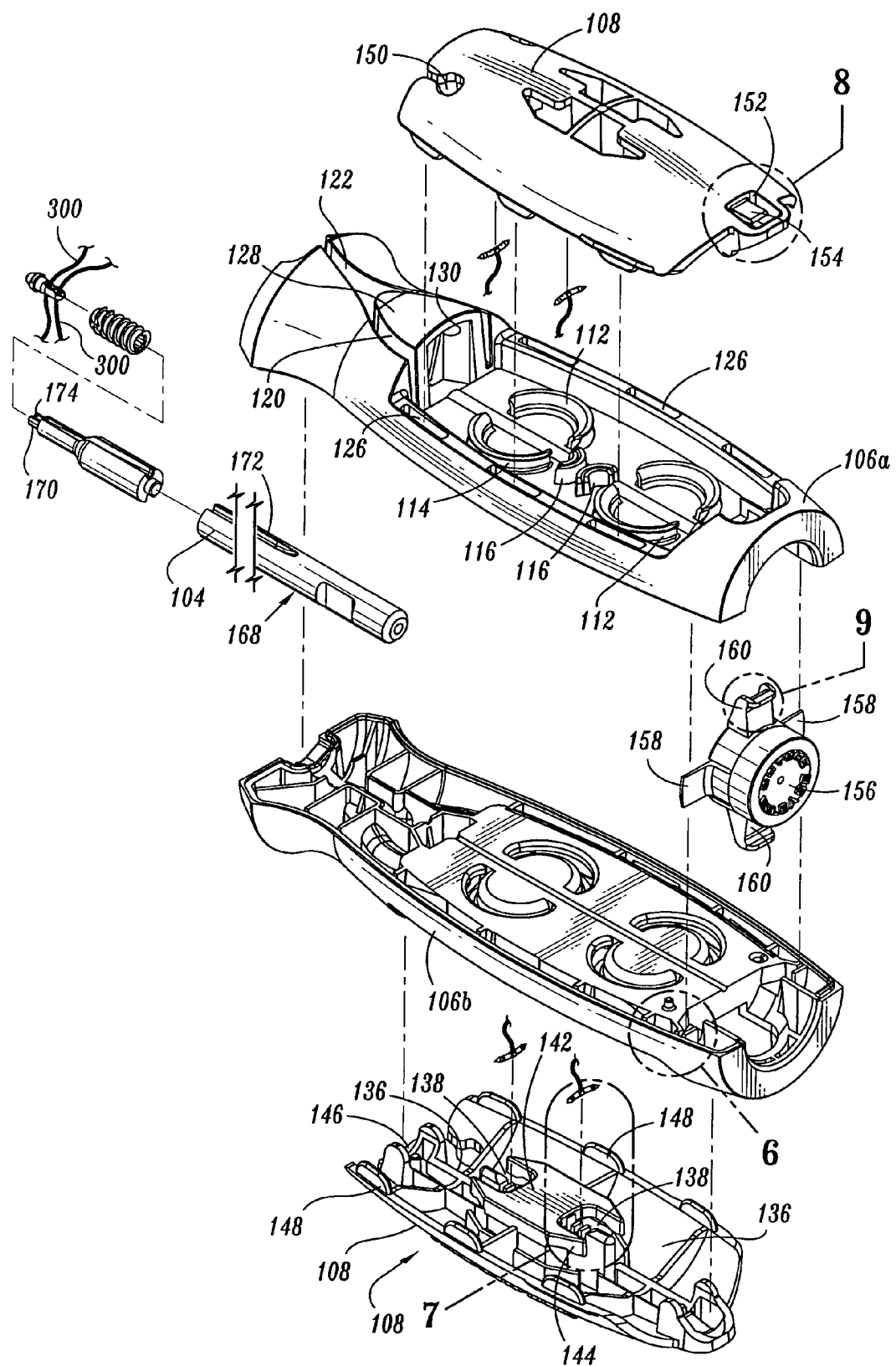
FIG. 2 is a perspective view with parts separated of the suture anchor installation system illustrating the installation tool, suture anchor and sutures with attached needles.

Referring now to FIGS. 1-2, there is illustrated the suture anchor installation system in accordance with the principles of the present disclosure. System 10 includes three main components, namely, installation apparatus or tool 100, suture anchor 200 releasably mounted to the tool 100 and sutures 300 which are connected to the suture anchor 200 and are at least partially housed within the installation tool 100.

Installation Tool 100

Figure 3:
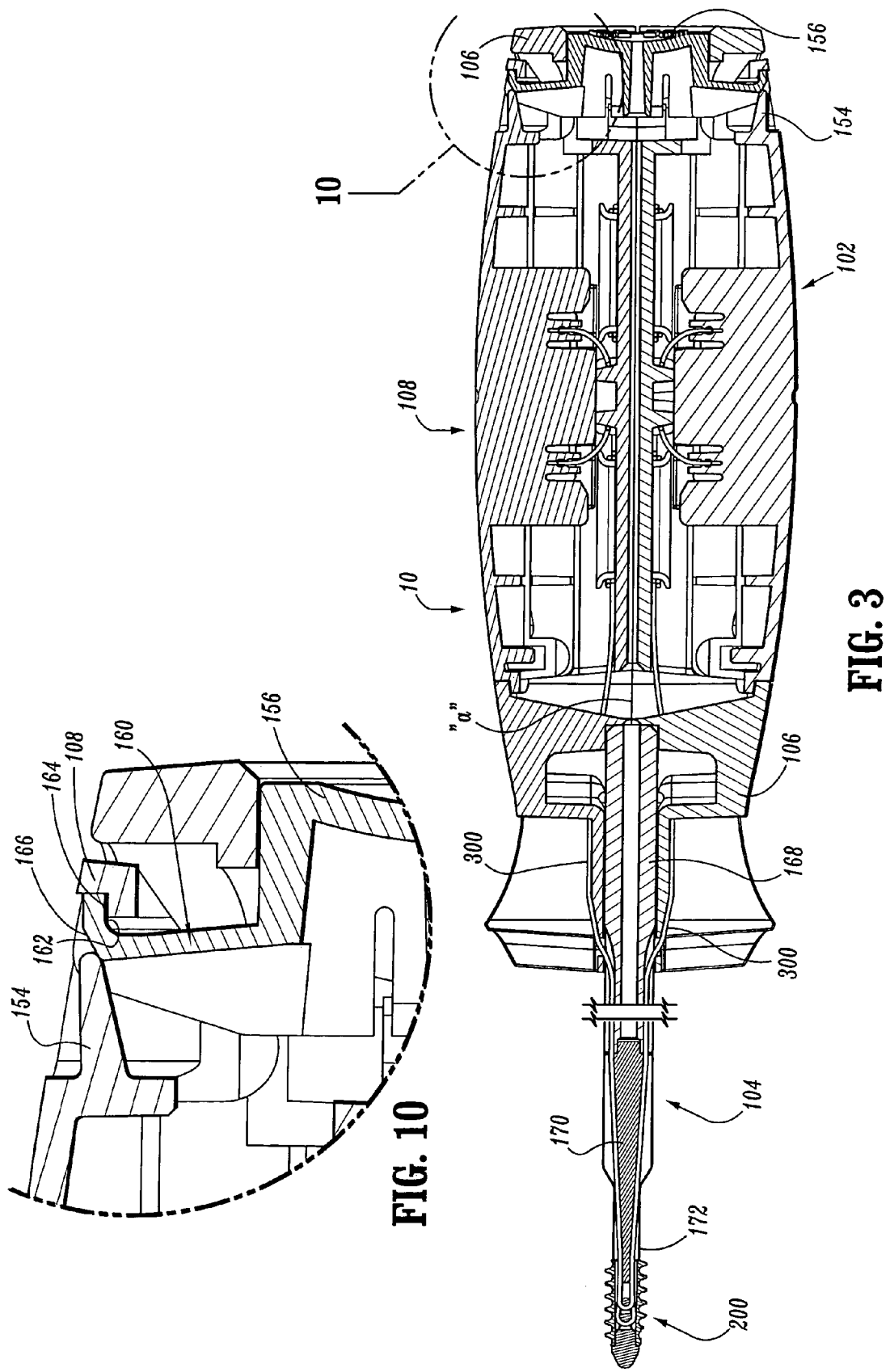
FIG. 3 is a side cross-sectional view of the suture anchor installation system.

With reference to FIGS. 1-3, installation tool 100 will now be described. Installation apparatus 100 includes handle 102 and elongated member 104 extending distally from the handle 102. Handle 102 includes frame 106 consisting of frame half sections 106a, 106b, and a pair of covers 108 which are releasably mounted to the respective frame sections 106a, 106b. Frame sections 106a, 106b are preferably fabricated from a suitable rigid polymeric material including, e.g., a polycarbonate or polystyrene, and formed through known injection molding techniques. Covers 108 may be fabricated from a transparent material, preferably a polymeric material. Alternately, frame half section 106a, 106b may be fabricated from a biocompatible metallic material including titanium, stainless steel and/or alloys thereof. Frame sections 106a, 106b are connected to each other with the use of ultrasonics, cement, adhesives, etc. Other means for connecting the frame sections 106a, 106b are also envisioned including snap fit arrangements, bayonet couplings, etc.

Figure 4:
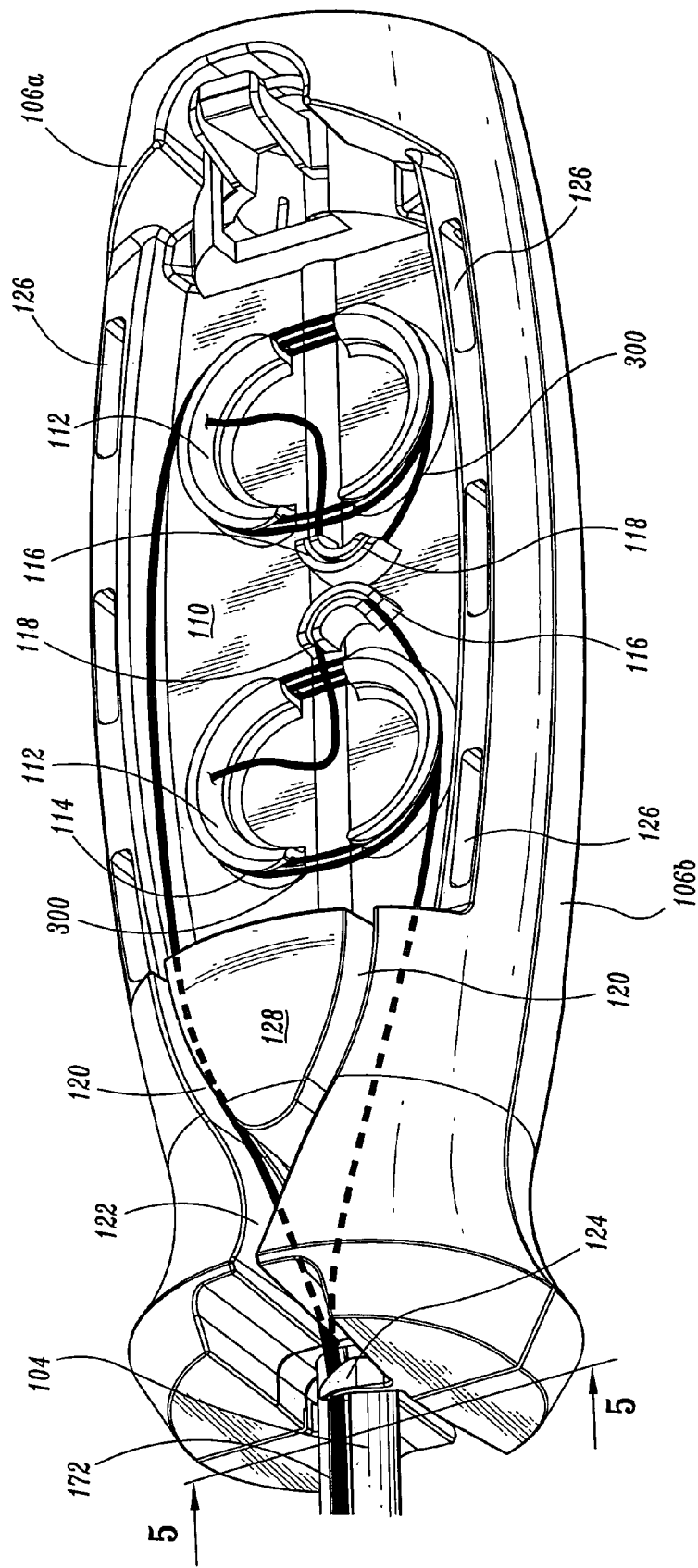
FIG. 4 is an enlarged perspective view of the handle of the installation tool.

Referring now to FIG. 4, in conjunction with FIGS. 1-3, each frame section 106a, 106b defines a central recessed area 110 over which cover 108 is positioned. Within each central recess area 110 is a pair of suture retainers or spools 112 disposed in adjacent side by side relation. Spools 112 face outwardly toward their respective covers 108 and away from the central longitudinal axis "a" of apparatus 10. Spools 112 are adapted to accommodate portions of suture 300 which are wound around the spools 112 in a coiled configuration. Specifically, each spool 112 defines an annular recess 114 to receive the wound sutures 300. Spools 112 are arranged to define an oval, racetrack or oblate configuration for receiving multiple revolution of sutures 300. Disposed between each pair of spools 112 of frame sections 106a, 106b is a pair of suture cleats 116, i.e., one cleat 116 for each spool 112. Cleats 116 each define channel 118 for receiving a portion of suture 300 extending from a corresponding spool 112. Generally, sutures 300 are preferably wrapped about spools 112 under tension and then passed under tension through a respective cleat 116 associated with the spool 112. Cleats 116 preferably serve as the primary tensioning means for suture 300 while spools 112 provide a secondary tensioning means.

Frame 106 further defines a pair of grooves 120 in the outer surface of each frame section 106a, 106b. Grooves 120 converge to single groove 122 adjacent the distal end of frame 106 and are adapted to accommodate the portions of sutures 300 extending to elongated member 104 and suture anchor 200.

Figure 5:
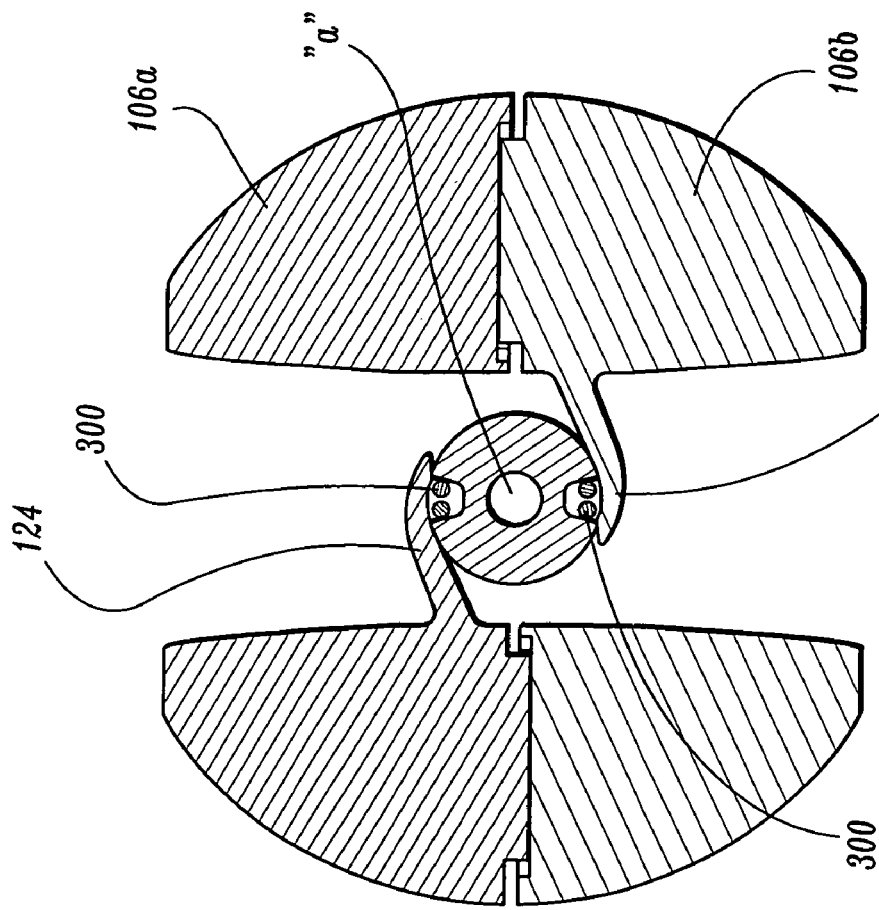
FIG. 5 is a cross-sectional view taken along the lines 5-5 of FIG. 4 illustrating the spring leafs for containing the sutures within the installation tool.

Referring now to FIGS. 4-5, frame 106 further includes a pair of spring leafs 124 disposed adjacent elongated member 104 in diametrical opposed relation. Spring leafs 124 are preferably in contacting relation with the elongated member 104. Spring leafs 124 are normally biased radially inwardly relative to longitudinal axis "a" and function to contain sutures 300 relative to elongated member 104. Spring leafs 124 may be separate components connected to frame 106 through conventional means. Preferably, spring leafs 124 are molded with frame 106 and incorporate the resiliency of the material of fabrication (e.g., the polymeric material) of frame 106 to normally engage elongated member 104. The functioning of leaf springs 124 will be discussed in greater detail hereinbelow.

Figure 6:
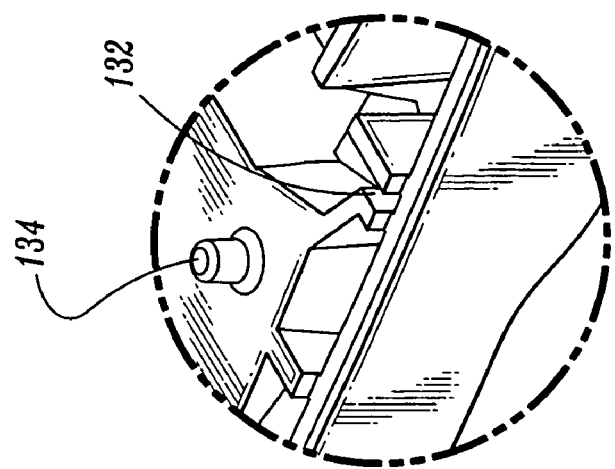
FIG. 6 is an enlarged isolated view illustrating the structure within the frame for mounting the release button.

Referring back to FIGS. 2 and 4, frame 106 further includes a plurality of slotted openings 126 disposed in a peripheral wall of each frame section 106a, 106b. Frame 106 also includes vertical enclosure 128 disposed within each half section 106a, 106b adjacent central recessed area 110. Vertical enclosures 128 define longitudinal locking surfaces 130. Slotted openings 126 and locking surfaces 130 assist in mounting covers 108 to frame 106. As best depicted in FIG. 6, in conjunction with FIG. 2, frame 106 further includes mounting slots 132 on each side of frame sections 106a, 106b and alignment posts 134. Alignment posts 134 coordinate alignment of frame sections 106a, 106b through reception within corresponding apertures (not shown) of the frame sections 106a, 106b during assembly.

Figure 7:
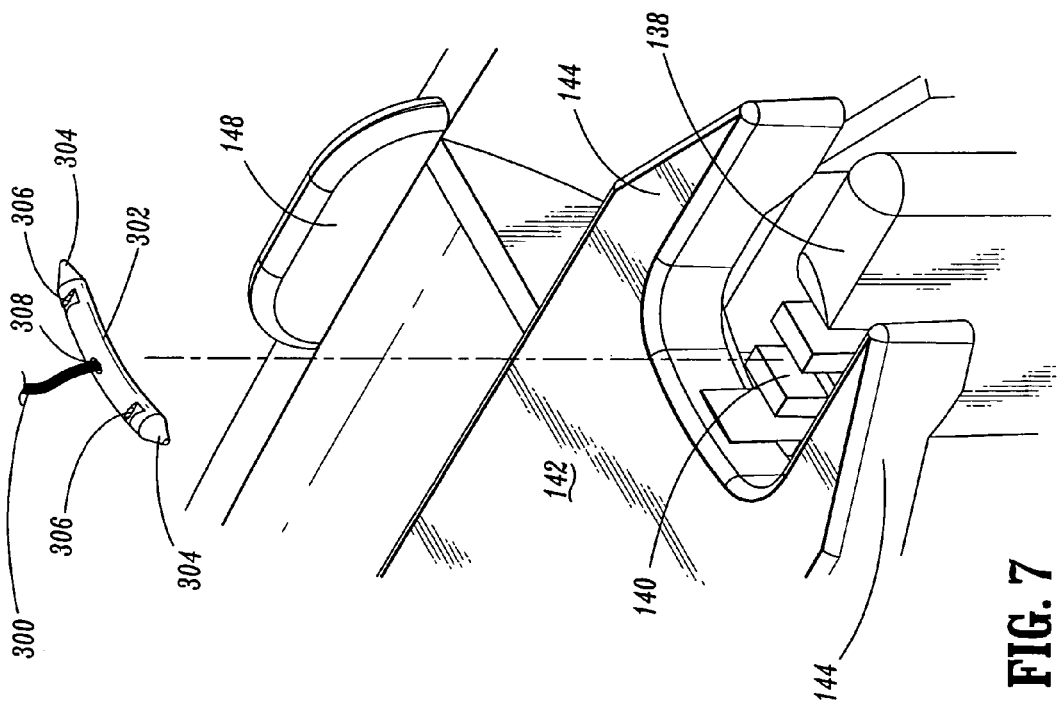
FIG. 7 is an enlarged isolated view of the needle retaining parks within the cover of the handle.

Referring now to FIGS. 2 and 7, covers 108 are adapted to be mounted to respective frame sections 106a, 106b. Each cover 108 is identical defining an internal surface 136 which faces respective frame sections 106a, 106b in the mounted condition of the cover 108. Covers 108 define internal needle parks 138 which are centrally located within the internal surfaces 136 of the covers 108. Two needle parks 138 are provided for each cover 108 and are generally located along the axis "a" of the apparatus 10. Needle parks 138 are adapted to receive a corresponding needle 302 attached to suture 300. Preferably, needle parks 132 include a channel 140 for receiving the needle 302 in frictional engagement therewith.

Referring still to FIGS. 2 and 7, covers 108 also each include guard 142 disposed between each needle park 132. Guards 142 entrap the suture portion within suture cleats 116 of frame 106 when in the assembled condition of cover 108 and frame 106 (see FIG. 2). Guard 142 defines a pair of alignment tabs 144 which extend to at least partially encompass each needle park 138. Alignment tabs 144 facilitate mounting and manipulation of needles 302 relative to a suturing apparatus as will be discussed. Cover 108 also includes distal tab 146 which is positioned within vertical enclosure 128 of frame 106 to engage locking surface 130 of the enclosure 128, and peripheral tabs 148 which are received within slotted openings 126 of the frame 106. Distal tab 146 and peripheral tabs 148 assist in mounting covers 108 to frame 106. Peripheral tabs 148 also serve to distribute forces to frame 106 upon rotation of handle 102 to minimize failure/breakage of the cover 108. Alternatively, covers 108 may be fixed to frame 106 with adhesives, tapes, snap-fit connection, or a press fit pin, etc.

Referring again to FIGS. 1 and 2, cover 108 further includes drape grabs 150 defined in the forward end of the cover 108. Drape grabs 150 define recesses which are advantageously dimensioned to receive and engage a surgical drape to permit the surgeon to hang cover 108 onto a surgical drape for subsequent use.

Figure 8:
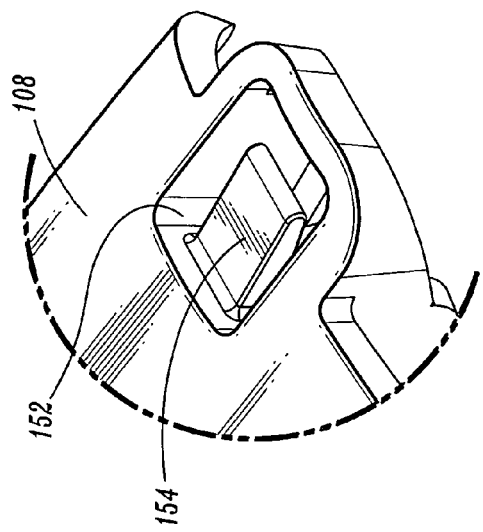
FIG. 8 is an enlarged isolated view of the latch opening and leaf spring within the cover.
Figure 9:
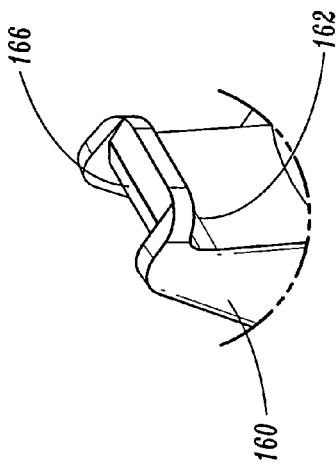
FIG. 9 is an enlarged isolated view illustrating the release latch of the release button.

With reference to FIG. 8, in conjunction with FIG. 2, cover 108 further includes latch opening 152 adjacent its proximal end and resilient leaf spring 154 within the latch opening 152. Leaf spring 154 is normally biased to the position depicted in FIG. 8, but is capable of deflecting radially outwardly against its inherent bias. The structure and function of leaf spring 154 will be discussed in greater detail hereinbelow.

Referring now to FIGS. 1-3 and 9-10, release button 156 will be discussed. Release button 156 is mounted within the rear or proximal end of frame 106. Release button 156 includes a pair of diametrically opposed mounting tabs 158. Mounting tabs 158 are recessed within corresponding mounting slots 132 (FIG. 6) of frame sections 106a, 106b to mount release button 156 to frame 106. Mounting tabs 158 are capable of deflecting to permit slight longitudinal movement of release button 156. Release button 156 further includes diametrically opposed release latches 160 extending radially outwardly relative to axis "a". Each release latch 160 defines a remote latch shelf 162 which engages a corresponding cover shelf 164 of cover 108 to secure the cover 108 relative to frame 106. Each release latch 160 also defines cam surface 166 extending continuously from latch shelf 162. In the assembled condition of cover 108, leaf spring 154 of cover 108 engages cam surface 166 to bias release latch 160 in a proximal and radially inward direction as depicted in FIG. 10. Consequently, latch shelf 162 is secured against cover shelf 164 of cover 108 thereby releasably locking the cover 108 to frame 106. Leaf springs 154 cause ejection or "pop-off" of covers 108 from frame 106.

Figure 11:
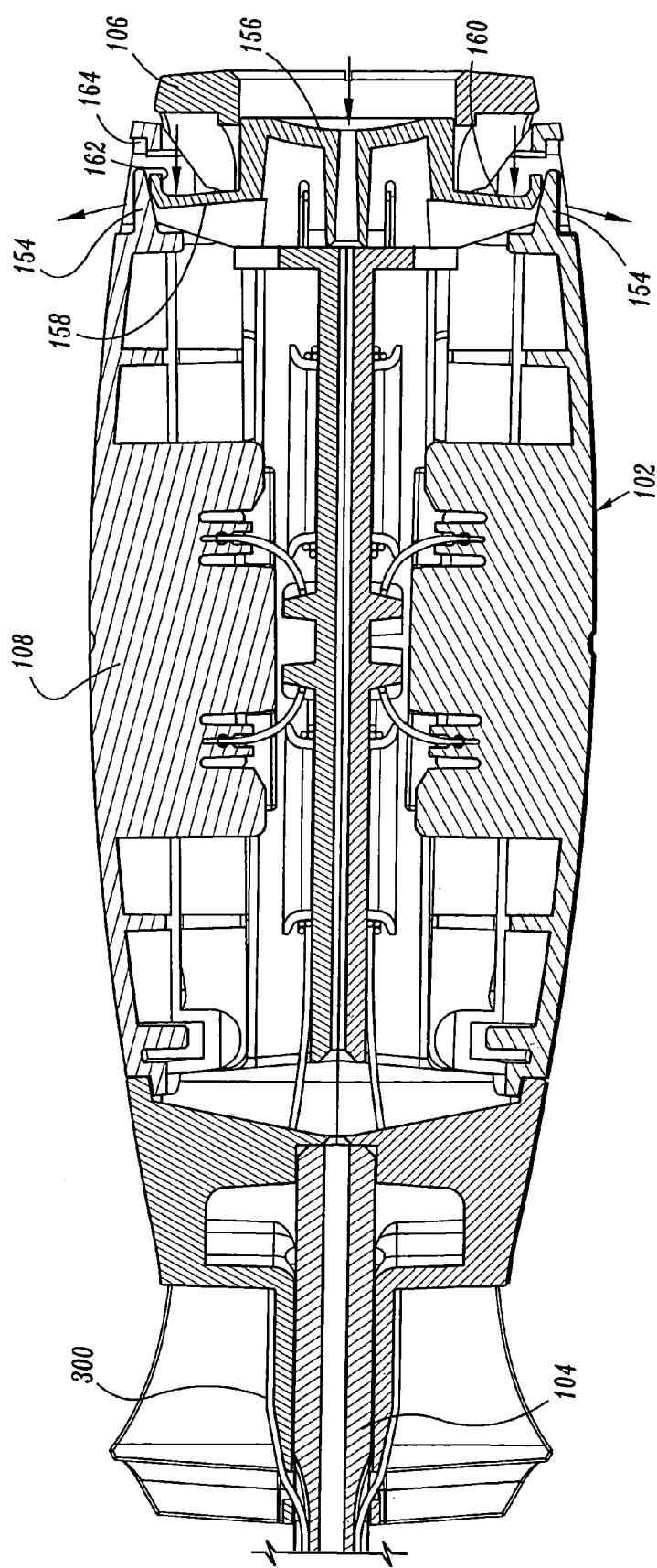
FIG. 11 is a cross-sectional view of the handle illustrating actuation of the release button and release of the cover.
Figure 12:
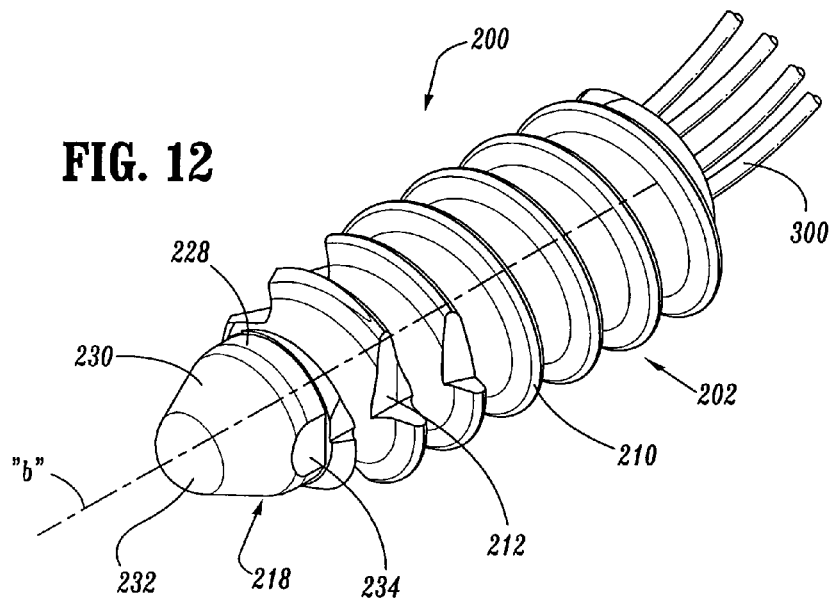
FIG. 12 is a perspective view of the suture anchor with attached sutures of the installation system of FIG. 1.

Release button 156 is adapted for limited longitudinal movement (as permitted by the deflection of mounting tabs 158) from a first unactuated position depicted in FIG. 3 to a second actuated position depicted in FIG. 11 to release release latches 160 from their engagement with cover 108. As shown in FIG. 3, depression of release button 156 causes release latches 160 to also distally advance. During this movement, cam surfaces 166 of release latches 160 displace leaf springs 154 in a general radial outward direction which permits the latches 160 to become released from engagement with cover shelf 164 of cover 108. Consequently, each cover 108 is expelled from frame 106 to expose sutures 300 and needles 302 within frame 106. Leaf springs 154 cause ejection or "pop-off" of covers 108 from frame 106. In particular, each leaf spring 154 is energized during initial advancement of release button 156, which causes radial deflection of the leaf springs 154. Further advancement of button 156 causes release of leaf springs 154 and release of the "energy" of the deformed or deflected leaf spring 154, consequently, causing an active ejection of covers 108.

Referring now to FIGS. 1-4, elongated member 104 will be discussed. Elongated member 104 includes hollow shaft 168 connected to handle 102 and anchor mount 170 which is connected to the distal end of shaft 168. Hollow shaft 168 may be connected to handle 102 by conventional means, e.g., with the use of adhesives, interference fit, mounting flanges, etc. Hollow shaft 168 includes a pair of longitudinal grooves 172 extending along its outer surface and along a major portion of the length of the hollow shaft 168. Longitudinal grooves 172 are disposed in diametrical opposed relation and are in communication with respective single grooves 122 in frame 106. Longitudinal grooves 172 accommodate sutures 300 extending from handle 102 to suture anchor 200. Shaft 168 may be a solid shaft if desired.

Anchor mount 170 is secured to hollow shaft 168 through a friction fit or the like. Anchor mount 170 also includes longitudinal grooves 174 within its outer surface aligned with longitudinal grooves 172 of hollow shaft 168. Longitudinal grooves 174 of anchor mount 170 accommodate sutures 300 extending from hollow shaft 168 to suture anchor 200. Anchor mount 170 defines distal mount end 176 for mounting suture anchor 300. Mount end 176 preferably defines a polygonal cross-section for reception within a corresponding polygonal bore of suture anchor 300 in frictional relation therewith. Accordingly, rotation of elongated member 104 causes corresponding rotation of suture anchor 300.

Although depicted as two separate components, hollow shaft 168 and anchor mount 170 may be a single component monolithically formed with the appropriate longitudinal grooves for reception of the sutures 300.

Suture Anchor

Figure 15:
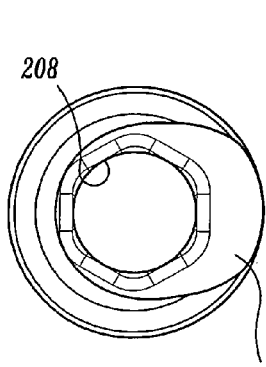
FIG. 15 is an axial view of the screw sleeve.
Figure 13:
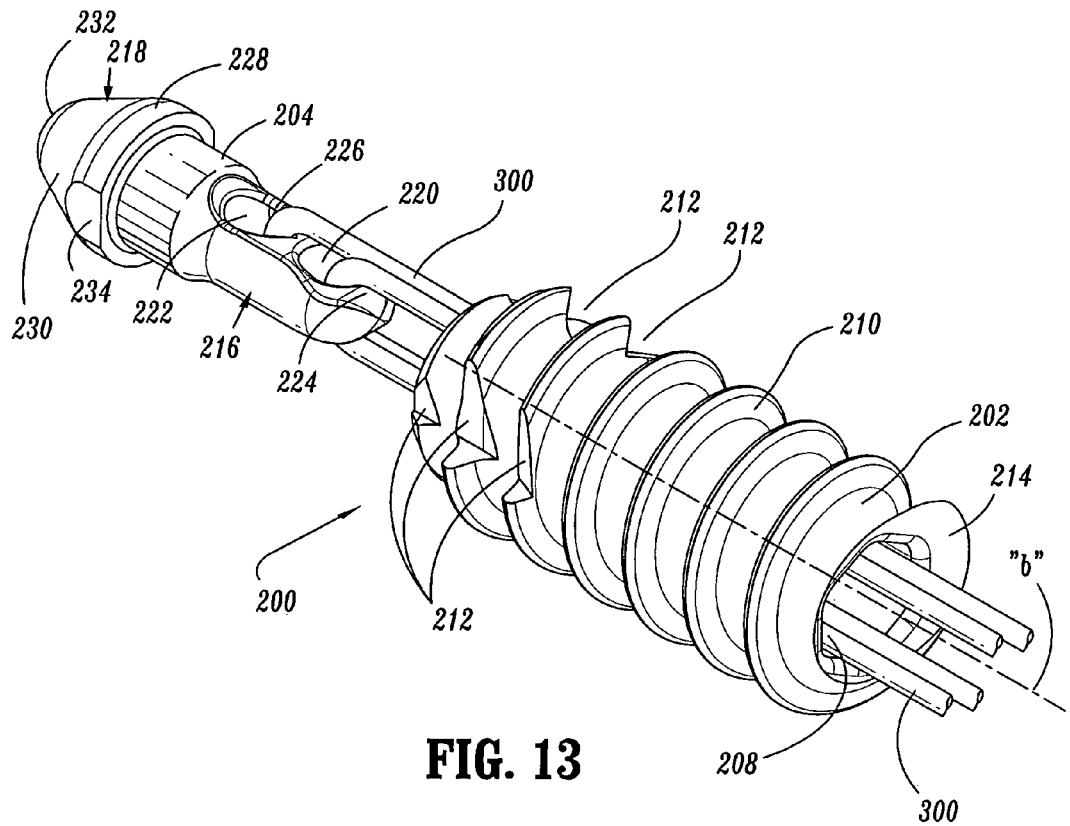
FIG. 13 is a perspective view with parts separated of the suture anchor illustrating the screw sleeve and the suture pin.

Referring now to FIGS. 12-15, suture anchor 200 will be discussed. Suture anchor 200 includes two components, namely, outer screw sleeve 202 and suture pin 204 which is positionable within the screw sleeve 202. Screw sleeve 202 defines longitudinal axis "b" and has longitudinal bore 206 extending the length of the sleeve 202. The proximal face of screw sleeve 202 defines a polygonal recess 208 (FIG. 13) e.g., a hexagon arrangement, for reception of mount end 176 of anchor mount 170 of tool 100. Screw sleeve 202 includes a threaded outer surface 210. Threaded outer surface 210 includes flutes or cut-outs 212 adjacent the distal end of screw sleeve 202. Flutes 212 provide a relief area for bone material removed during the insertion of suture anchor 200. As best depicted in FIGS. 13 and 15, screw sleeve 202 includes a recessed or arcuate face 214 (as opposed to a straight edge or face) in its proximal end. Arcuate face 214 is dimensioned to receive the suture ends subsequent to insertion of suture anchor 200 within bone. Specifically, in ligament repair, the sutures may be loaded with tension at an angle to the axis of the anchor 200. Thus, in this application, arcuate face 214 would receive the sutures 300a, 300b which are loaded at the angle. Additionally, the rounded non-traumatic contour of arcuate face 214 advantageously minimizes the potential of severance of the sutures 300.

Suture pin 204 includes pin shaft 216 and pin head 218 adjacent the distal end of the pin shaft 216. Pin shaft 216 includes a pair of transverse bores 220, 222 for receiving the looped sutures 300. Pin shaft 216 further defines grooves 224, 226 (FIG. 13) in its outer surface contiguous with respective transverse bores 220, 222 and extending in a proximal direction. Grooves 224, 226 accommodate portions of sutures 300 extending from suture anchor 200 back to tool 100. In a preferred embodiment, the diameter or cross-section of the portion of pin shaft 216 containing transverse bore 222 is greater than a corresponding cross-section of a portion of the pin shaft 216 containing transverse bore 220. With this arrangement, the suture 300 received within transverse bore 222 is slightly outwardly displaced relative to the suture received within bore 220. This arrangement minimizes the potential of entanglement of the sutures 300 and facilitates sliding of sutures 300 within suture anchor 200.

Pin head 218 defines proximal collar section 228 of constant diameter and distal conical section 230. Distal conical section 230 terminates in rounded end surface 232. Pin head 218 further includes a pair of chamfers or flats 234 defined in its outer surface, specifically, extending through collar section 228 to the proximal end of conical section 230. Chamfers 234 are arranged in diametrical opposed relation as shown. Chamfers 234 may be positioned to be in general longitudinal alignment with flutes 212 of outer screw sleeve 202 when suture pin 204 is oriented within the screw sleeve 202. However, longitudinal alignment of chamfers 234 and flutes 212 is not necessary to achieve the objects of the present disclosure. Chamfers 234 also assist in manufacture and assembly of suture anchor 200 by presenting a generally flat surface for reception within a fixture or chuck during, e.g., loading of sutures 300. Chamfers 234 may also provide relief zones during insertion and/or self tapping of suture anchor 200 within tissue to collect bone or tissue material displaced during the insertion process, preferably, during initial insertion. The presence of chamfers 234 also may reduce the profile of pin head 218 thereby facilitating passage of suture anchor 200 through tissue.

Figure 16:
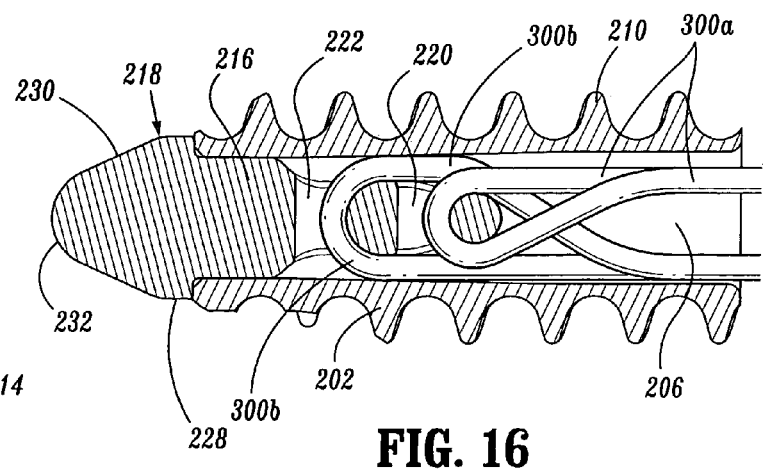
FIG. 16 is a side cross-sectional view of an alternate embodiment of the suture anchor.
Figure 14:
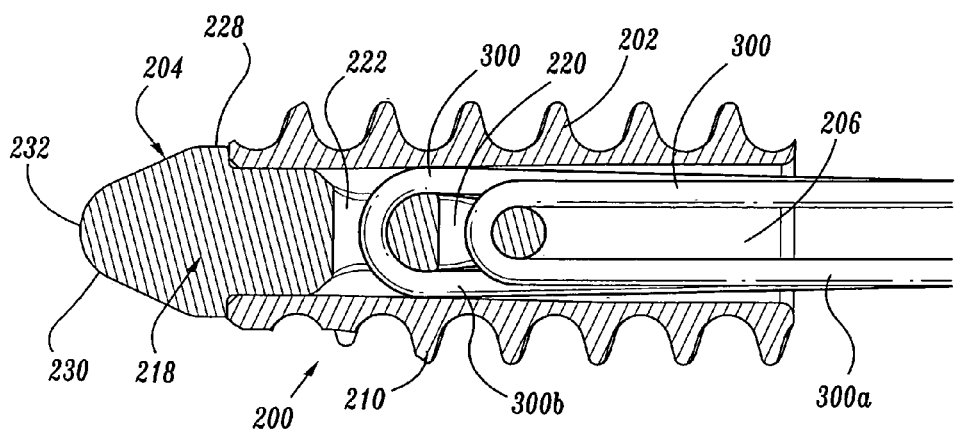
FIG. 14 is a side cross-sectional view of the suture anchor.

In a preferred method of arrangement depicted in FIG. 14, a pair of sutures 300a, 300b is passed though respective transverse bores 220, 222 to define suture loops extending from suture anchor 200 to insertion tool 100. The end of the sutures 300a, 300b are then directed into corresponding longitudinal grooves 172,174 of hollow shaft 168 and anchor mount 170, and routed into handle 102 in the aforedescribed manner. With this arrangement, each longitudinal groove 172, 174 accommodates a length of suture of each suture 300a, 300b. In the alternative, as depicted in FIG. 16, the suture ends are arranged whereby each end of an individual suture 300a, 300b is routed to a respective single longitudinal groove 172, 174, i.e., a single longitudinal groove 172 accommodates the suture ends of a single suture thereby substantially isolating the sutures 300a, 300b from each other. This arrangement may minimize the potential of entanglement of the sutures 300a, 300b.

Suture anchor 200 may be fabricated from a biocompatible metal including stainless steel, titanium and/or alloys thereof. Alternatively, suture anchor 200 may be fabricated from a synthetic bioabsorbable polymeric resin such as polymers of glycolide, lactide, caprolactone, p-dioxone, trimethylbone carbonate and physical and/or chemical combination thereof.

Sutures

Referring now to FIG. 4, the arrangement of sutures 300 within insertion tool 100 and suture anchor 200 will be discussed. First and second sutures 300a, 300b are loaded in insertion tool 100 and suture anchor 200. Each suture 300a, 300b has an attached needle 302 at both ends of sutures 300a, 300b. The preferred needle 302 is disclosed in the commonly assigned U.S. Pat. No. 5,478,344 to Stone, the entire contents of which are incorporated herein by reference. As best depicted in FIG. 7, needle 302 is a double ended needle having pointed ends 304 and a pair of recesses 306 positioned adjacent each pointed end 304. The end of the suture 300 is received within central aperture 308 of needle 302 and retained therein with adhesives, glues, crimping or any other conventional means. As an alternative, sutures 300 may be devoid of needles 302.

Each suture 300a, 300b is passed through a respective transverse bore 220, 222 of suture pin 204 and routed through longitudinal grooves 174 of anchor mount 170 and longitudinal grooves 172 of hollow shaft 168 in the manner discussed hereinabove in connection with the discussion of the embodiment of FIG. 14, or, alternatively, the embodiment of FIG. 16. Each end of the suture loop of respective sutures 300a, 300b are wrapped or coiled under tension about a respective spool 112 within handle 102 and passed through a corresponding suture cleat 116. Suture cleat 116 preferably securely engages the suture portion. The procedure is performed for all sutures 300a, 300b with each frame section 106a, 106b. The needles 302 attached to each suture end are mounted to the corresponding needle parks 138 in covers 108 (FIG. 2). Covers 108 are then mounted to their respective frame sections 106a, 106b.

Sutures 300 may be fabricated from any non-absorbable or absorbable material including nylon, polyesters, etc. or any of the materials of fabrication of suture anchor 200 identified hereinbelow and may or may not be coated with a suitable coating.

Suturing Apparatus

Figures 17, 22:
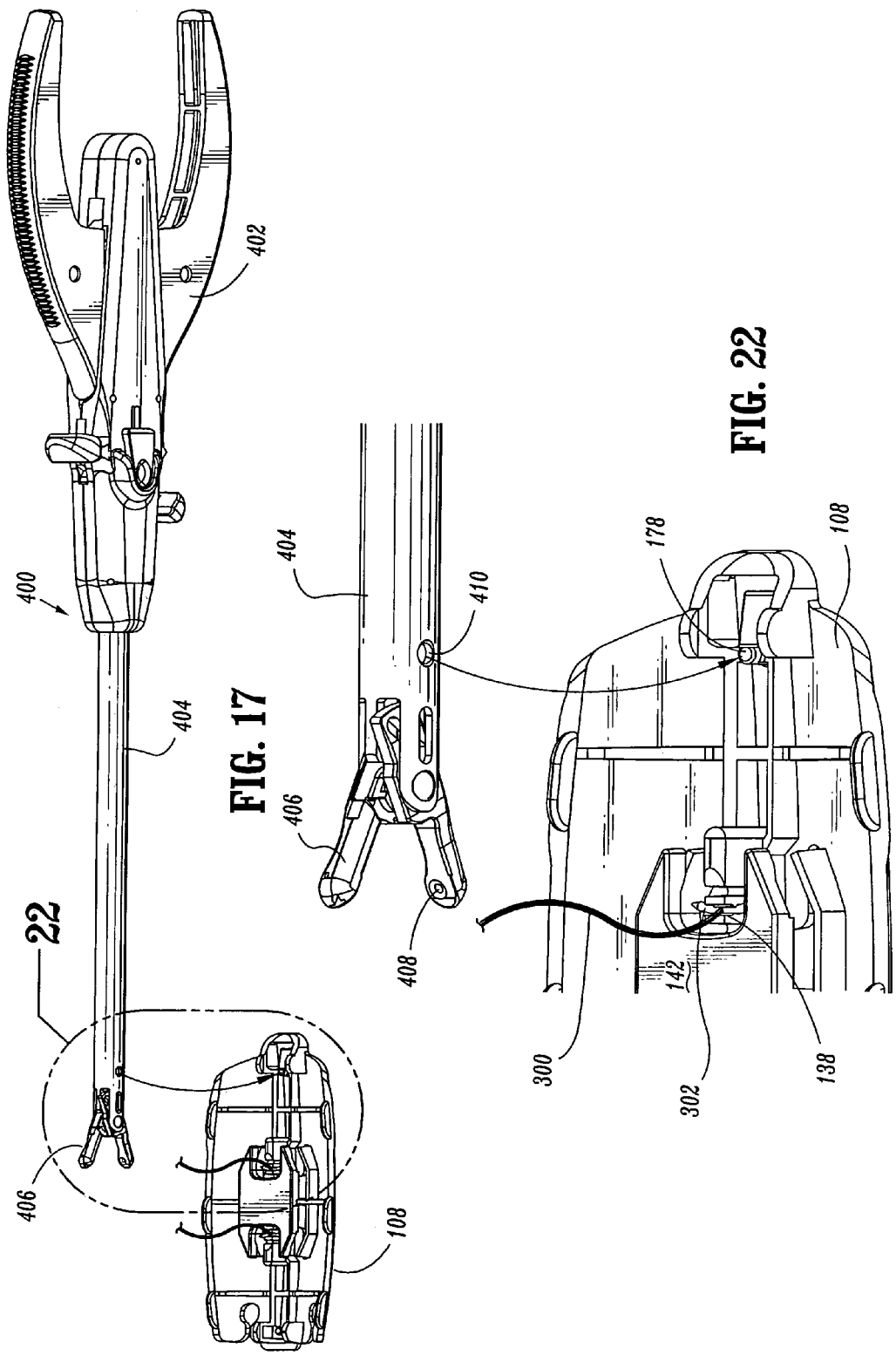
FIG. 17 is a perspective view of a suturing apparatus for use with the installation system.
FIG. 22 is an enlarged isolated view illustrating the relationship of the jaws of the suturing apparatus of FIG. 17 and the needle park of the insertion tool.

FIG. 17 illustrates a suturing apparatus which may be used with insertion apparatus of FIG. 1. Suturing apparatus 400 is disclosed in the afore-mentioned commonly assigned U.S. Pat. No. 5,478,344 to Stone. Suturing apparatus 400 includes handle 402 and elongated member 404 extending from the handle 402. A pair of jaws 406 is pivotally mounted to the distal end of elongated member 404. Jaws 406 include recesses 408 for receiving respective needle ends 304 of suturing needle 302. Generally jaws 406 open and close to pass the needle 302 between the jaws 406 and through tissue in alternating manner. Thus, needle 302 draws suture 300 through tissue to suture the tissue and eventually secure the suture 300, tissue and suture anchor 200. Further details of structure and operation of suture apparatus 400 may be ascertained by reference to the '344 patent.

Operation of Suture Anchor Installation System 10

Figure 18:
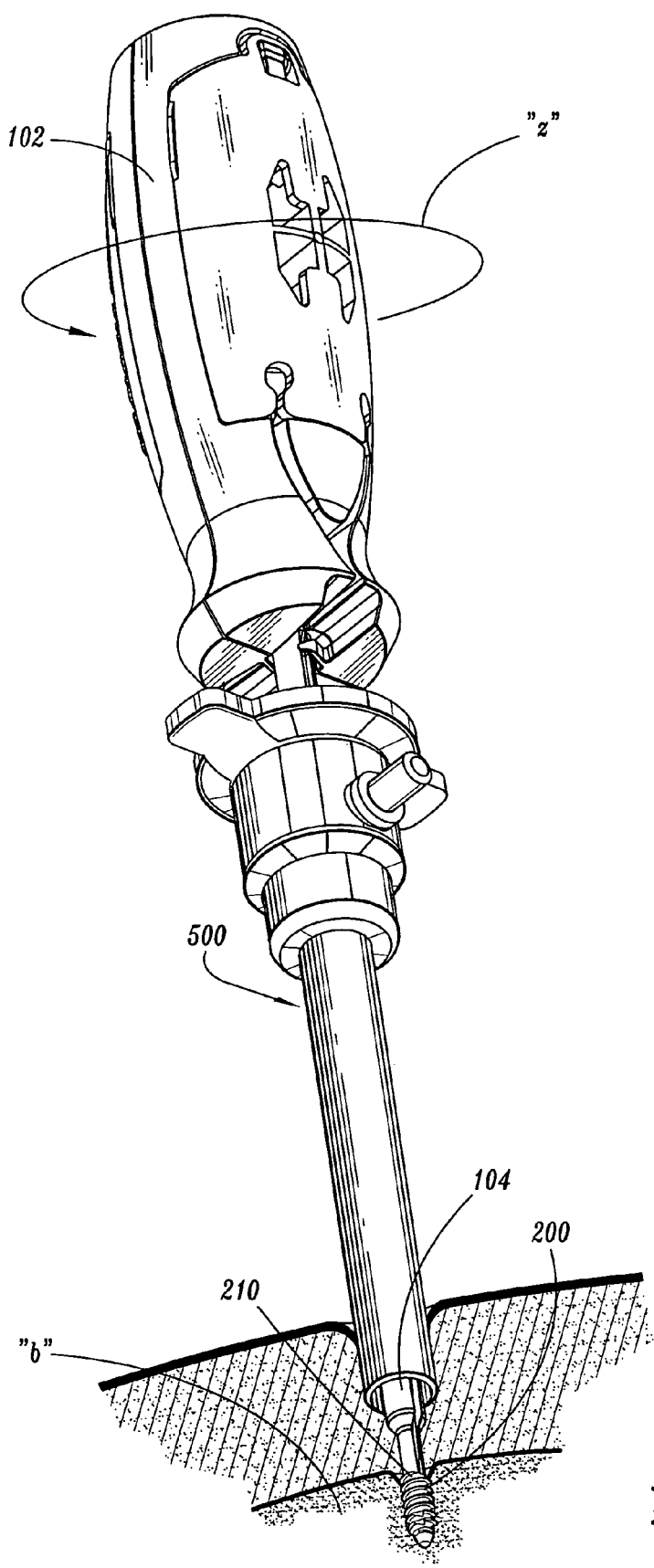
FIG. 18 is a view illustrating endoscopic insertion of the installation system through a cannula accessing a tissue site.

The use of the suture anchor installation system 10 in conjunction with an endoscopic surgical procedure will be discussed. With reference to FIG. 18, an underlying tissue site is accessed with cannula 500 through conventional endoscopic means to provide direct communication with the tissue site. In laparoscopic procedures, the abdominal cavity is insufflated with insufflation gases to raise the cavity wall to permit unrestricted access to the tissue site. In arthroscopic applications, the targeted area, e.g., joint (such as knee, shoulder or elbow) may be supplied with fluids to distend the joint. Thereafter, insertion tool 100 with mounted suture anchor 200 and sutures 300 are introduced into the cannula 500 and advanced toward the tissue (e.g., bone) site. Suture anchor 200 is implanted within the appropriately sized pre-drilled bore in the bone "b" by rotation of insertion tool 100 in the direction of directional arrow "z". Such rotation causes corresponding rotation of screw anchor 200 which causes threaded outer surface 210 of screw sleeve 202 to engage the body tissue and advance within the bore of the bone. The bore within the bone "b" may be tapped prior to insertion of the anchor 200 or screw sleeve 202 may be self tapping.

Figure 20:
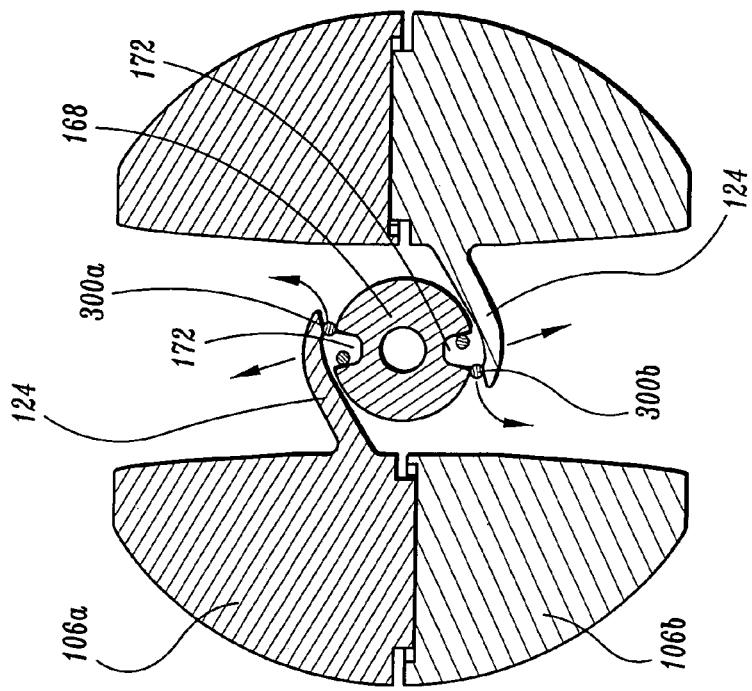
FIG. 20 is a cross-sectional view similar to the view of FIG. 5 illustrating release of the sutures from the spring leafs of the insertion tool.
Figure 19:
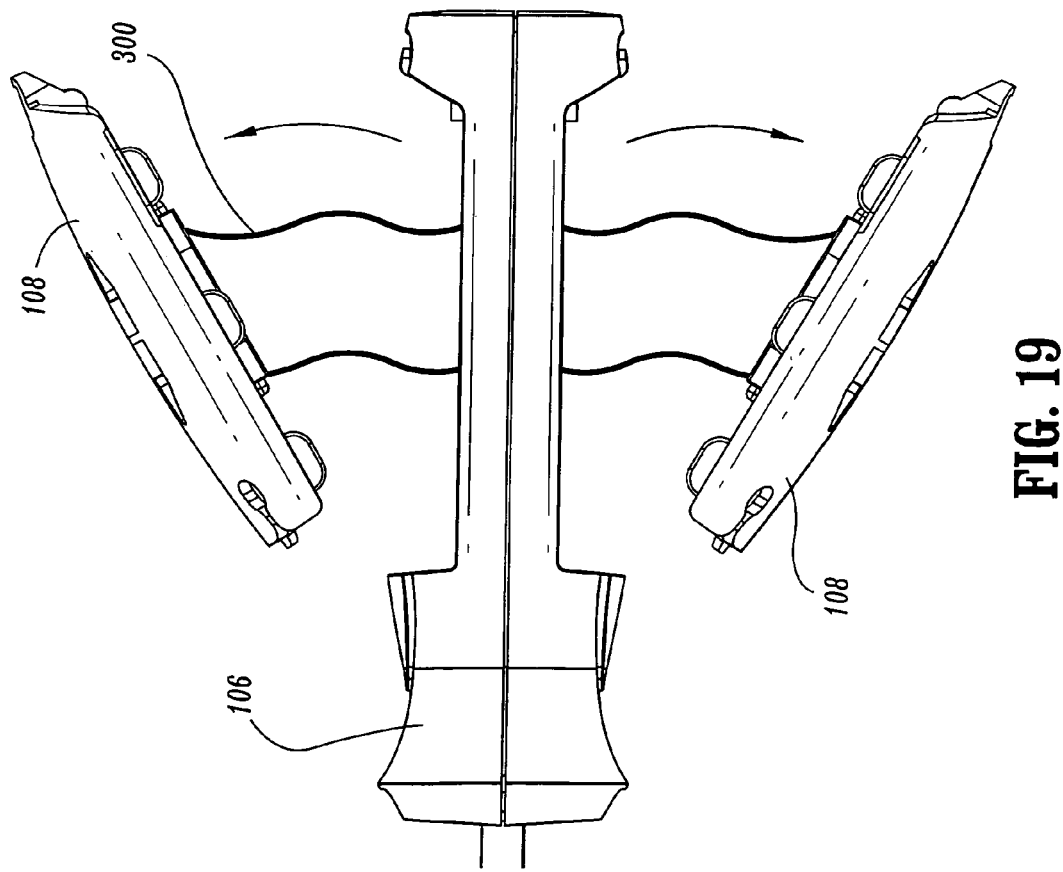
FIG. 19 is a view illustrating release of the covers from the frame of the insertion tool.
Figure 21:
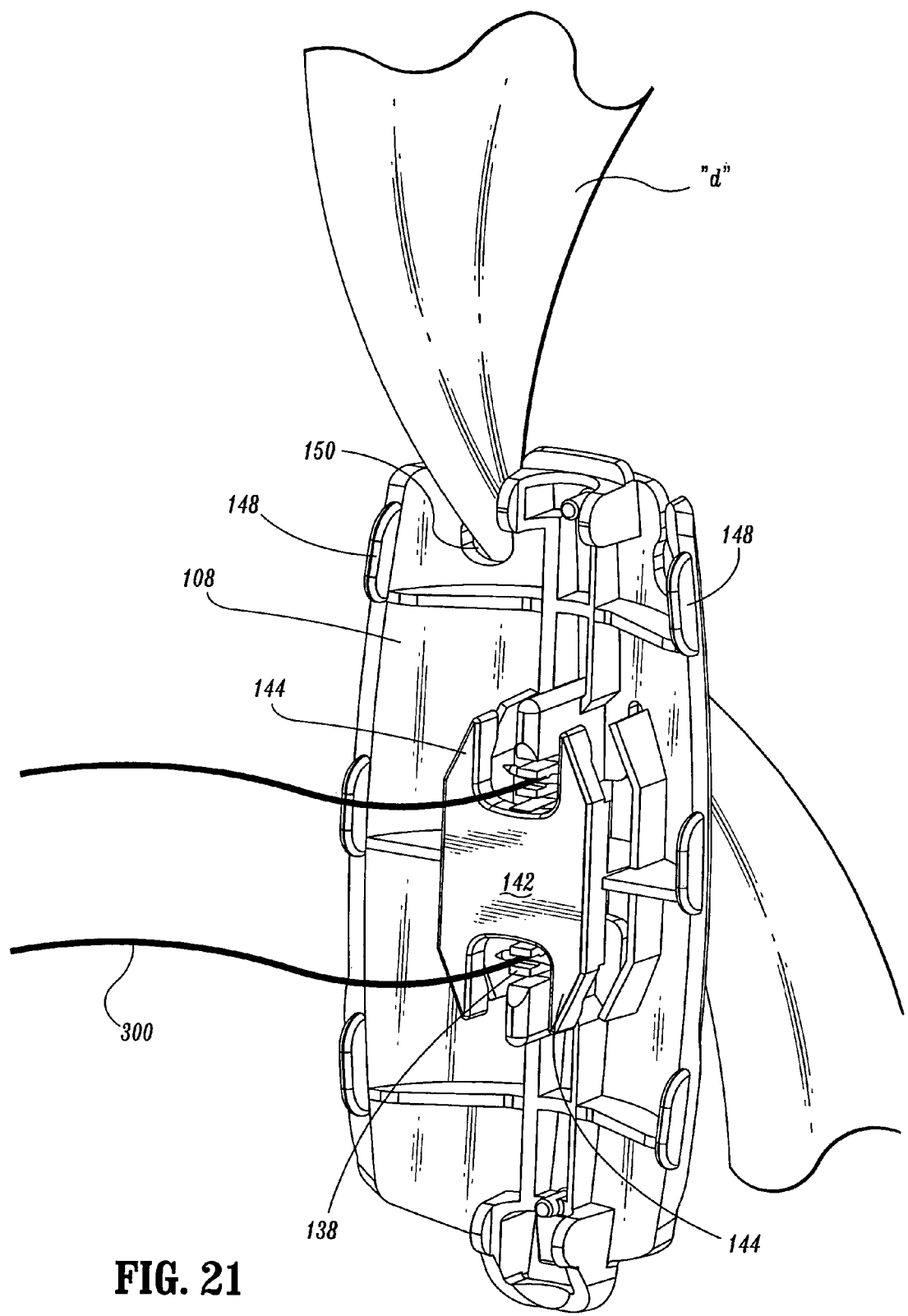
FIG. 21 is a view illustrating securement of the cover of the insertion tool on a drape in the surgical area.

The procedure is continued by actuating release button 156 which causes covers 108 to be released in the manner discussed in connection with FIG. 11. FIG. 19 depicts covers 108 removed from frame 106. Installation tool 100 is then removed from trocar 500. As illustrated in FIG. 20, sutures 300a, 300b are able to be released from longitudinal grooves 172 of hollow shaft 168 through deflection of spring leafs 124 of frame 106. Covers 108 may be mounted to a surgical drape "d" if desired by reception of drape portions within drape grabs 150 as depicted in FIG. 21.

Referring now to FIG. 22, suturing apparatus 400 is then positioned with respect to cover 108 to load needle 302 in the apparatus 400. In a preferred embodiment, suturing apparatus 400 includes opening 410 in elongate member 404. Suturing apparatus 400 is positioned whereby opening 410 receives post 178 of cover 108. As shown in FIG. 23, jaws 406 are then positioned to engage alignment tabs 144 of cover 108 to appropriately orientate jaws 406 of suturing apparatus 400 with respect to needles 302 within needle park 138 of cover 108. As depicted in FIG. 24, it is also contemplated that guard 142 adjacent needle parks 138 may include enlarged thickened sections 180 within alignment tabs 144 which cooperate with arcuate surfaces 412 of jaws 406 of suturing apparatus 400. The presence of thickened sections 180 and arcuate surfaces 412 of jaws 406 ensure that jaws 406 are properly loaded with respect to the needle park 138.

Suturing apparatus 400 is actuated to close at least one of the jaws 406 such that the one jaw 406 receives and engages a needle end 304 of needle 302 within recess 408. Needle 302 which is now connected to the one jaw 406 of apparatus 400 is then removed from needle park 138. Suturing apparatus 400 is utilized in the aforedescribed manner to stitch the tissue and/or prosthetic implant relative to the hard bone. The sutures 300 may be tied down to the bone tissue and bone anchor. This procedure may be repeated for the remaining three needles 302 within covers 108.

Alternate Embodiment(s)

Figure 25:
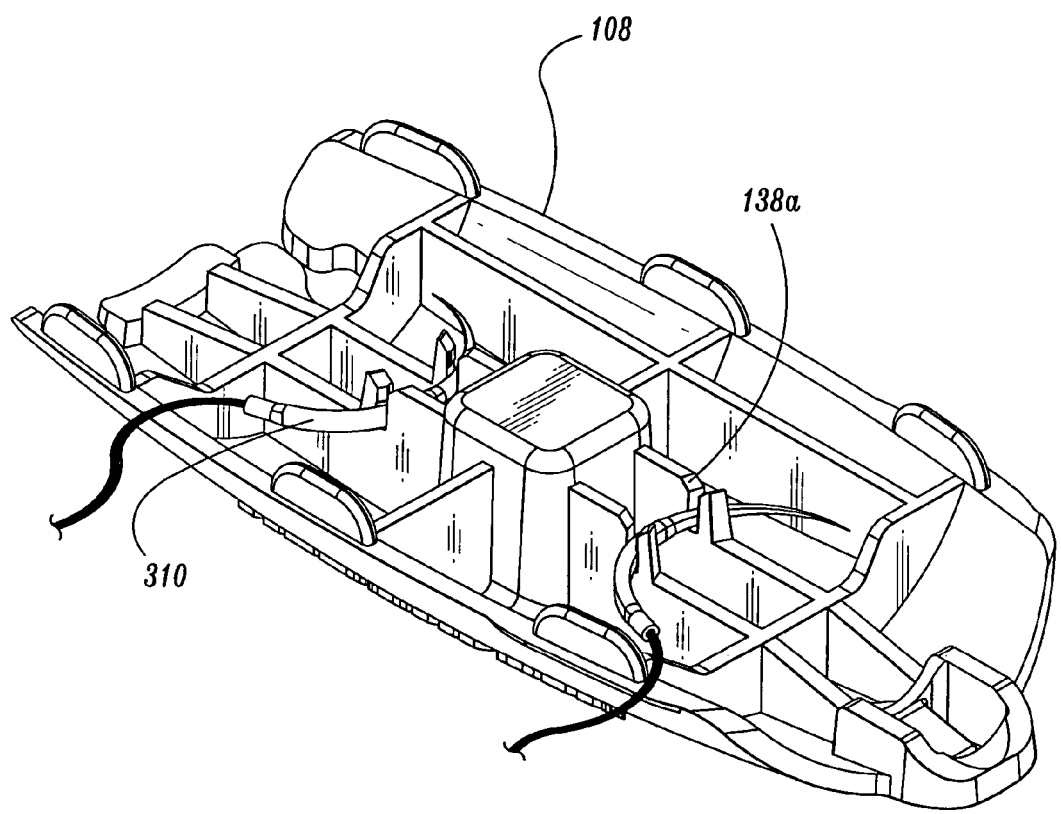
FIG. 25 is a perspective view of an alternate embodiment of the cover of the installation tool.

FIG. 25 illustrates an alternate embodiment of cover 108 of handle 102. In accordance with this embodiment, cover 108 is devoid of guard 142. Needle parks 138a are adapted to receive conventional surgical needles 310. This embodiment of the suture anchor installation system is preferably used during a conventional open procedure without the use of suturing apparatus 400.

FIG. 26-27 illustrate an alternate embodiment of frame 106. In accordance with this embodiment, second cleats 182 are provided on each frame section 106a, 106b. Second cleats 182 are adapted to securely engage sutures 300a, 300b extending from elongated member 104. In this regard, second cleats 182 tension sutures 300a, 300b before the sutures 300a, 300b are wrapped about spools 112 and positioned within first cleats 116. Second cleats 182 provide a more direct and higher degree of tension on the suture portions 300a, 300b extending to suture anchor 200. Second cleats 182 incorporate a pair of posts 184 spaced to grab at least one or more the suture portions 300.

Figure 28:
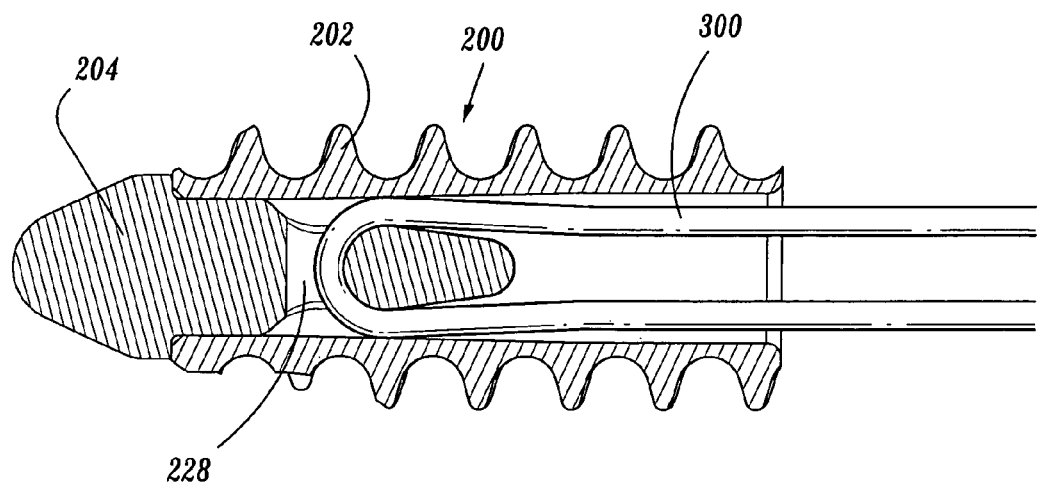
FIG. 28 is a side cross-sectional view of a alternate embodiment of the suture anchor.

FIG. 28 illustrates an alternate embodiment of suture anchor 200. In accordance with this embodiment, suture pin 204 includes a single transverse bore 228 for receiving a single loop of suture 300. In this application, handle 102 incorporates one cover 108 and one central recessed area 110 with corresponding spools 112.

Figure 30:
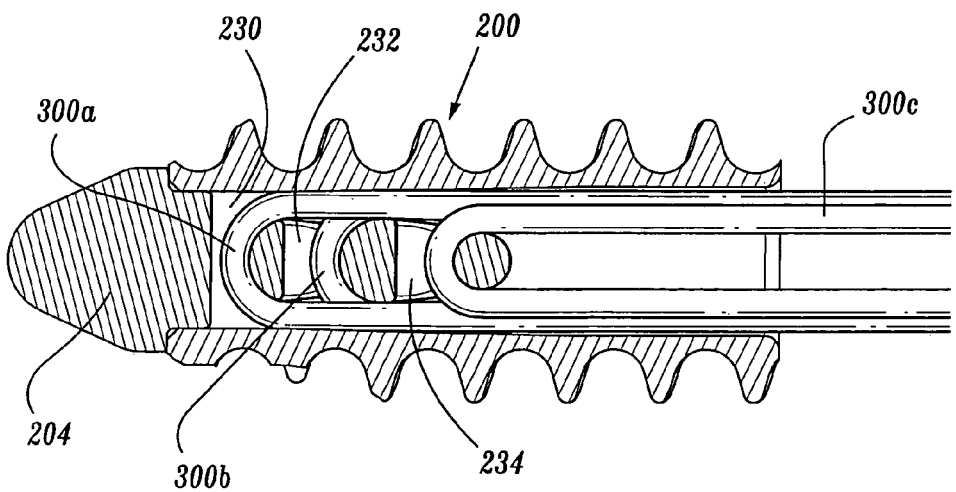
FIG. 30 is a cross-sectional view taken along the lines 30-30 of FIG. 29.
Figures 29, 31:
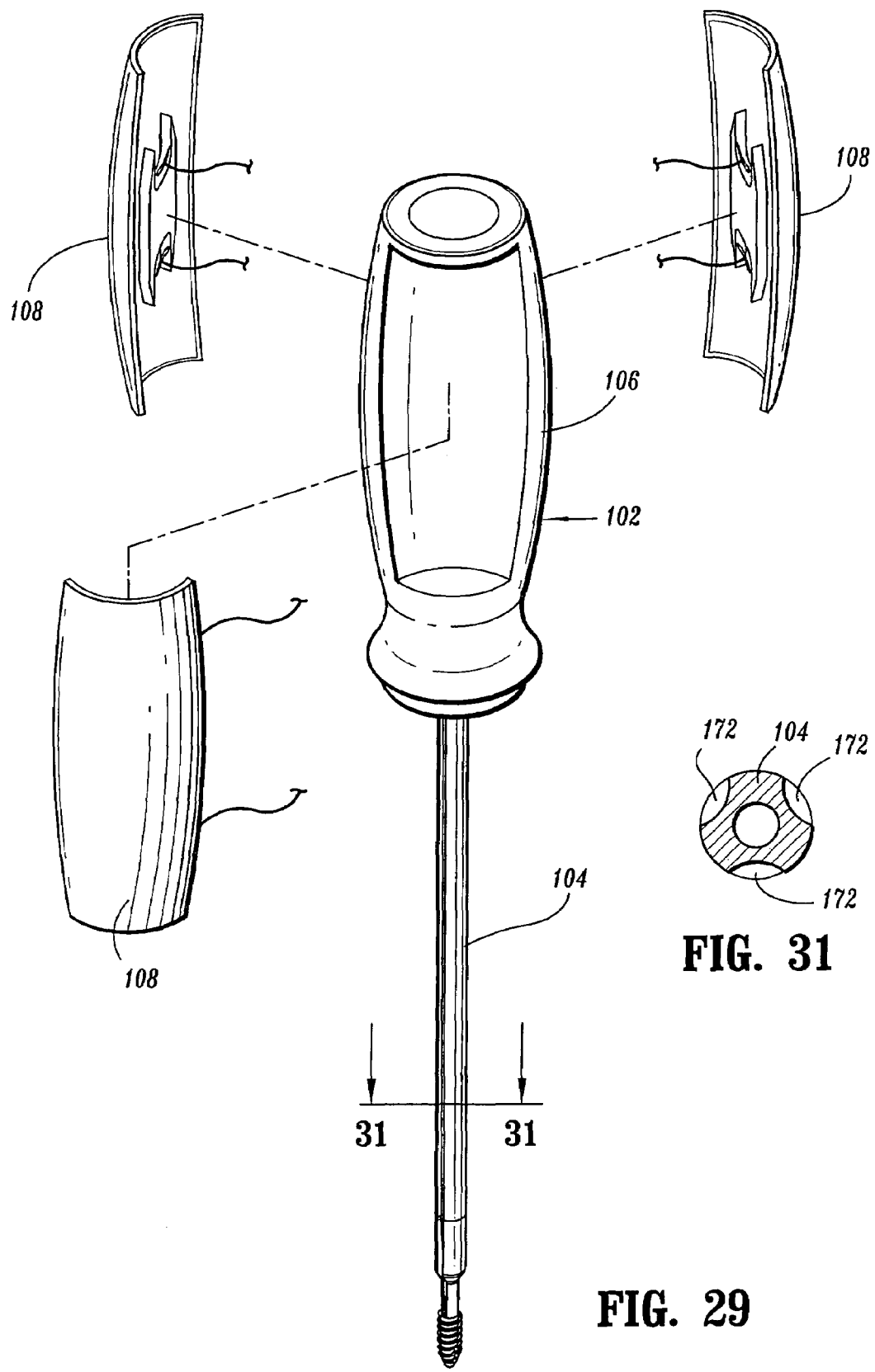
FIG. 29 is a perspective view of an alternate embodiment of the suture anchor installation system.
FIG. 31 is a cross-sectional view of the suture anchor for use with the system of FIG. 29.

FIGS. 29-31 illustrate another alternate embodiment of the suture anchor installation system 10. In accordance with this embodiment, installation tool 100 incorporates three central recessed areas 110 with corresponding pair of spools 112 within each area 110 of handle 102. Similarly, handle 102 also includes three corresponding covers 108 mountable to frame 206 for enclosing recessed areas 110. Elongated member 104 includes three external longitudinal grooves 172 for accommodating the three sets of sutures 300. Suture anchor 200 includes suture pin 204 having three transverse bores 230, 232, 234 for accommodating sutures 300a, 300b, 300c. In all other respects, the system operates in the same manner as the embodiment of FIG. 1.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

We claim:

1. An apparatus for placement of a suture anchor having a suture connected thereto, which comprises:
   a handle dimensioned for engagement by a user, the handle including:
   a frame having a suture retainer adapted for retaining a suture; and
   at least one cover releasably mounted to the frame to at least partially enclose the suture retainer, the at least one cover including an interior surface and an exterior surface;
   an elongated member connected to the handle and extending therefrom, and defining a longitudinal axis, the elongated member having an anchor mount for mounting a suture anchor; and
   an internal needle park integral with the interior surface of the at least one cover such that the needle park is releasably mounted relative to the frame, and being adapted for retaining at least one needle, the needle park disposed within an interior of the handle when the at least one cover is mounted to the frame, wherein release of the at least one cover from the frame exposes the internal needle park to permit access to the at least one needle retained therein.

2. The apparatus according to claim 1 including a release button mounted to the frame and movable to release the at least one cover from the frame to expose the suture portion.

3. The apparatus according to claim 2 wherein the handle includes a latch operatively connected to the release button, the latch being released upon movement of the release button.

4. The apparatus according to claim 3 wherein the latch is engageable with a locking shelf of the at least one cover in a first unactuated position of the release button to secure the at least one cover to the frame.

5. The apparatus according to claim 4 wherein the latch is adapted to release the locking shelf upon movement of the release button to a second actuated position thereof.

6. The apparatus according to claim 5 wherein the at least one cover includes a leaf spring adapted to bias the latch into engagement with the locking shelf in the first unactuated position of the release button.

7. The apparatus according to claim 6 wherein the release button includes a camming surface, engageable with the leaf spring upon movement of the release button to the second actuated position to permit release of the locking shelf.

8. The apparatus according to claim 6 wherein the leaf spring is adapted to eject the cover in at least a general radial outward direction upon movement of the release button to the second actuated position.

9. The apparatus according to claim 1 wherein the at least one cover includes a drape grab for engaging a portion of a surgical drape to facilitate securement of the at least one cover to the surgical drape.

10. The apparatus according to claim 1 wherein the suture retainer of the frame includes a spool wherein the suture portion is wrapped about the spool.

11. The apparatus according to claim 1 wherein the elongated member includes at least one longitudinal groove for accommodating a suture portion extending to the suture anchor mounted to the anchor mount of the elongated member.

12. The apparatus according to claim 11 wherein the elongated member includes first and second longitudinal grooves.

13. The apparatus according to claim 1 including a suture anchor and at least one suture extending from the suture anchor, the suture anchor being releasably secured to the anchor mount of the elongated member, the at least one suture extending along the elongated member and engagable with the suture retainer of the frame.

14. The apparatus according to claim 13 including a needle connected to the at least one suture, the needle releasably secured to the needle park within the at least one cover.

15. The apparatus according to claim 1 wherein the handle includes:
   first and second suture retainers for retaining first and second suture portions;
   first and second covers releasably mounted to the frame for at least partially enclosing respective first and second suture retainers; and
   a release button mounted to the handle, wherein the release button is movable to release each of the first and second covers.

16. The apparatus according to claim 2 including means for releasably securing the cover to the frame and wherein the release button is adapted to release the securing means.

17. An apparatus for placement of a suture anchor having a suture connected thereto, which comprises:
   a handle dimensioned for engagement by the user, the handle including:
   a frame having first and second opposed frame sections, each frame section having a suture retainer adapted for retaining a suture portion;
   first and second covers releasably mounted to respective first and second frame sections to at least partially enclose the suture retainers, each cover having an internal needle park integral with an internal surface thereof such that the needle park is releasably mounted relative to the frame, each internal needle park adapted for retaining a needle; and
   a release button mounted to the frame and movable to simultaneously release both the first and second covers to expose the suture portions; and
   an elongated member connected to the handle and extending therefrom, the elongated member having an anchor mount for mounting a suture anchor.

18. The apparatus according to claim 13 wherein the suture anchor includes:
   an outer sleeve having a threaded portion and defining a longitudinal axis; and
   an inner suture pin positionable within the outer sleeve, the suture pin including first and second bores for receiving respective first and second sutures, the bores each defining a bore axis extending in transverse relation to the longitudinal axis.

19. The apparatus according to claim 18 wherein the suture pin includes grooves formed in an outer surface thereof and extending from respective transverse bores, the grooves dimensioned to accommodate suture portions extending from the transverse bores.

20. The apparatus according to claim 19 wherein the bore axes of the first and second bores are in general parallel relation to each other.

21. The apparatus according to claim 18 wherein the suture pin includes first and second pin sections having the first and second bores respectively, the first pin section defining a cross-sectional dimension greater than the second pin section.

22. The apparatus according to claim 18 wherein the threaded portion of the outer sleeve includes flutes defined therein.

23. The apparatus according to claim 18 wherein the inner suture pin includes a pin head and a pin shaft, the pin shaft having the first and second bores and at least partially positionable in the outer sleeve, the pin head having at least one chamfer defined in an outer surface thereof.

24. The apparatus according to claim 23 wherein the pin head includes a pair of chamfers arranged in general diametrical opposed relation.

25. The apparatus according to claim 2 wherein the release button is adapted for general longitudinal movement and is slidable relative to the frame.

26. The apparatus according to claim 15 including first and second sutures connected to the suture anchor and having respective first and second needles connected thereto, the first needle releasably secured to a first internal needle park in the first cover and the second needle connected to a second internal needle park in the second cover.

27. The apparatus according to claim 17 wherein the handle includes first and second latches, the first and second latches operatively connected to the release button.

28. The apparatus according to claim 27 wherein the first and second latches are configured and adapted to releasably engage with a corresponding latch shelf of the first and second covers respectively when the release button is in a first unactuated position, to thereby secure the first and second covers to the frame.

29. The apparatus according to claim 28 wherein each of the first and second latches is adapted to release the respective latch shelf upon movement of the release button to a second actuated position thereof.

30. The apparatus according to claim 29 wherein the first and second covers each include a leaf spring adapted to bias the respective first and second latches into engagement with the latch shelf in the first unactuated position of the release button.

31. The apparatus according to claim 30 wherein each of the first and second latches includes a camming surface configured to engage the respective leaf spring upon movement of the release button to the second actuated position to permit release of the respective latch shelf.

32. The apparatus according to claim 31 wherein the camming surfaces of each of the first and second latches is configured to displace the respective leaf spring in a radially outward direction upon movement of the release button to the second actuated position.

33. The apparatus according to claim 30 wherein each leaf spring is adapted to eject the respective cover in a radially outward direction upon movement of the release button to the second actuated position.

34. The apparatus according to claim 17 wherein the release button is adapted for general longitudinal movement.

* * * * *

UNITED STATES PATENT AND TRADEMARK OFFICE
CERTIFICATE OF CORRECTION

PATENT NO. : 7,645,293 B2  Page 1 of 1
APPLICATION NO. : 11/108269
DATED : January 12, 2010
INVENTOR(S) : Martinek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 592 days.

Signed and Sealed this

Sixteenth Day of November, 2010

David J. Kappos
*Director of the United States Patent and Trademark Office*